United States Patent
Johnson et al.

(10) Patent No.: US 12,161,621 B2
(45) Date of Patent: Dec. 10, 2024

(54) METHODS FOR FRUCTOKINASE MEDIATION OF ALCOHOL CRAVING AND ALCOHOL INDUCED LIVER DISEASE

(71) Applicant: REGENTS OF THE UNIVERSITY OF COLORADO, A BODY CORPORATE, Denver, CO (US)

(72) Inventors: Richard J. Johnson, Centennial, CO (US); Miguel A. Lanaspa-Garcia, Denver, CO (US); Sondra Bland, Erie, CO (US)

(73) Assignee: THE REGENTS OF THE UNIVERSITY OF COLORADO

( * ) Notice: Subject to any disclaimer, the term of this patent is extended or adjusted under 35 U.S.C. 154(b) by 932 days.

(21) Appl. No.: 17/261,279

(22) PCT Filed: Jul. 16, 2019

(86) PCT No.: PCT/US2019/042034
§ 371 (c)(1),
(2) Date: Jan. 19, 2021

(87) PCT Pub. No.: WO2020/046481
PCT Pub. Date: Mar. 5, 2020

(65) Prior Publication Data
US 2021/0275494 A1    Sep. 9, 2021

Related U.S. Application Data

(60) Provisional application No. 62/698,468, filed on Jul. 16, 2018.

(51) Int. Cl.
*A61K 31/37* (2006.01)
*A61K 45/06* (2006.01)
(Continued)

(52) U.S. Cl.
CPC .............. *A61K 31/37* (2013.01); *A61K 45/06* (2013.01); *A61P 1/16* (2018.01); *A61P 25/32* (2018.01)

(58) Field of Classification Search
CPC ...... A61K 31/37; A61K 45/06; A61K 31/713; A61K 36/00; A61P 1/16; A61P 25/32
See application file for complete search history.

(56) References Cited

U.S. PATENT DOCUMENTS

| 9,387,245 B2 * | 7/2016 | Johnson ............... A61K 31/427 |
| 2013/0209484 A1 * | 8/2013 | Garcia ................. A61K 31/155 514/52 |

(Continued)

FOREIGN PATENT DOCUMENTS

| WO | 2012019188 A2 | 2/2012 | |
| WO | WO-2014008351 A2 * | 1/2014 | .......... A61K 31/045 |
| WO | 2020046481 A2 | 3/2020 | |

OTHER PUBLICATIONS

Protective effect of quercetin on alcohol abstinence-induced anxiety and convulsions, J. Med. Food, 8, pp. 392-396, by Joshi et al. (Year: 2005).*

(Continued)

*Primary Examiner* — Jeffrey S Lundgren
*Assistant Examiner* — Alexander K. Showalter
(74) *Attorney, Agent, or Firm* — MARSHALL, GERSTEIN & BORUN LLP

(57) ABSTRACT

The invention relates to the use of one or more fructokinase (ketohexokinase) (KHK) inhibitors to both prevent and treat a wide variety of diseases including, but not limited to, alcohol craving, alcohol addiction, alcohol induced liver disease including a fatty liver and cirrhosis.

2 Claims, 3 Drawing Sheets
Specification includes a Sequence Listing.

(51) Int. Cl.
    *A61P 1/16*     (2006.01)
    *A61P 25/32*     (2006.01)

(56) References Cited

U.S. PATENT DOCUMENTS

2014/0072662 A1    3/2014    Ciccocioppo
2020/0071331 A1    3/2020    Durham

OTHER PUBLICATIONS

Effects of Quercetin on Expression of Genes of Carbohydrate and Lipid Metabolism Enzymes in the Liver of Rats Receiving High-Fructose Ration, Bull. Exp. Biol. Med, 167, pp. 263-266, by Mzhel'skaya et al. (Year: 2019).*
Points to Consider in Drug Development of Biologics and Small Molecules, available at the time of this writing at the url https://www.allucent.com/resources/blog/points-consider-drug-development-biologics-and-small-molecules (Year: 2023).*
Pathogenesis and Management of Alcoholic Liver Disease, Dig. Dis., 34, 3pgs. 47-355, by Farooq et al. (Year: 2016).*
Toshikuni et al., Clinical differences between alcoholic liver disease and nonalcoholic fatty liver disease, World J. Gastroenterol., 20, pp. 2393-8406 (Year: 2014).*
Farooq et al., Pathogenesis and Management of Alcoholic Liver Disease, Dig. Dis., 34, pp. 47-355 (Year: 2016).*
PCT/US2019/042034, PCT Search Report &Written Opinion , Mailed Jul. 16, 2019, 14 pages.
Beier, Juliane I. et al., "Mechanisms and cell signaling in alcoholic liver disease", Biol Chem., Nov. 2010, vol. 391, No. 11, pp. 1249-1264.
European Association for the Study of the Liver Clinical Practical Guidelines: "Management of Alcoholic Liver Disease", Journal of Hepatology, 2012, vol. 57, pp. 399-420.
Futatsugi, Kentaro et al., "Discovery of PF-06835919: A Potent Inhibitor of Ketohexokinase (KHK) for the Treatment of Metabolic Disorders Driven by the Overconsumption of Fructose", J. Med. Chem., Sep. 10, 2020, 59 pages.
Futatsugi, Kentaro et al., "Discovery of PF-06835919: A Potent Inhibitor of Ketohexokinase (KHK) for the Treatment of Metabolic Disorders Driven by the Overconsumption of Fructose", Supporting Information, Sep. 10, 2020, 42 pages.
Gao, Bin et al., "Alcoholic Liver Disease: Pathogenesis and New Therapeutic Targets", Gastroenterology, Nov. 2011 , vol. 141, No. 5, pp. 1572-1585.
Gibbs, Alan C. et al., "Electron Density Guided Fragment-Based Lead Discovery of Ketohexokinase Inhibitors", J. Med. Chem. 2010, vol. 53, pp. 7979-7991.
Hajnal, Andras et al., "Oral sucrose stimulation increases accumbens dopamine in the rat", Am J Physiol Regul Integr Comp Physiol, 2004, vol. 286, pp. R31-R37.
Huard, Kim et al., "Discovery of Fragment-Derived Small Molecules for in Vivo Inhibition of Ketohexokinase (KHK)", J. Med. Chem. 2017, vol. 60, pp. 7835-7849.
Jensen, Thomas et al., "Fructose and Sugar: A Major Mediator of Nonalcoholic Fatty Liver Disease", J Hepatol, May 2018, vol. 68, No. 5, pp. 1063-1075.
Ko, Ben C. B. et al., "Identification and Characterization of Multiple Osmotic Response Sequences in the Human Aldose Reductase Gene", The Journal of Biological Chemistry, 1997, vol. 272, No. 26, Issue of Jun. 27, pp. 16431-16437.
Le, MyPhuong T. et al.,"Bioactivity-Guided Identification of Botanical Inhibitors of Ketohexokinase", PLoS One, Jun. 20, 2016, vol. 11, No. 6, 7 pages.
Lustig, Robert H.,"Fructose: It's Alcohol Without the Buzz", American Society for Nutrition. Adv. Nutr., 2013, vol. 4, pp. 226-235.
Maryanoff, Bruce E. et al.,"Pyrimidinopyrimidine inhibitors of ketohexokinase: Exploring the ring C2 group that interacts with Asp-27B in the ligand binding pocket", Bioorganic & Medicinal Chemistry Letters, 2012, vol. 22, pp. 5326-5329.
Maryanoff, Bruce E. et al.,"Inhibitors of Ketohexokinase: Discovery of Pyrimidinopyrimidines with Specific Substitution that Complements the ATP-Binding Site", ACS Med. Chem. Lett., 2011, vol. 2, pp. 538-543.
Most, Dana et al., "Molecular basis of alcoholism", Handb Clin Neurol., 2014, vol. 125, pp. 89-111.
Rada, P. et al., "Daily Bingeing on Sugar Repeatedly Releases Dopamine in the Accumbens Shell", Neuroscience, 2005, vol. 134, pp. 737-744.
Shi, Changxuan et al., "Inhibition of aldose reductase ameliorates alcoholic liver disease by activating AMPK and modulating oxidative stress and inflammatory cytokines", Molecular Medicine Reports, 2017, vol. 16, pp. 2767-2772.
Softic, Samir et al., "Divergent effects of glucose and fructose on hepatic lipogenesis and insulin signaling", The Journal of Clinical Investigation, Mar. 2018, vol. 128, No. 3, p. 1199.
Softic, Samir et al., "Divergent effects of glucose and fructose on hepatic lipogenesis and insulin signaling", The Journal of Clinical Investigation, Nov. 2017, vol. 127, No. 11, pp. 4059-4074.
Tang, Wai Ho et al., "Aldose reductase, oxidative stress, and diabetic mellitus", Frontiers in Pharmacology, May 2012, vol. 3, Article 87, 8 pages.
Thomes, Paul G. et al., "Dietary fructose augments ethanol-induced liver pathology", Journal of Nutritional Biochemistry, 2017, vol. 43, pp. 141-150.
Westwater, Margaret L. et al., "Sugar addiction: the state of the science", Eur J Nutr, 2016, vol. 55, pp S55-S69.
Zhang, Xuqing et al., "Optimization of a pyrazole hit from FBDD into a novel series of indazoles as ketohexokinase inhibitors", Bioorganic & Medicinal Chemistry Letters, 2011, vol. 21, pp. 4762-4767.

* cited by examiner

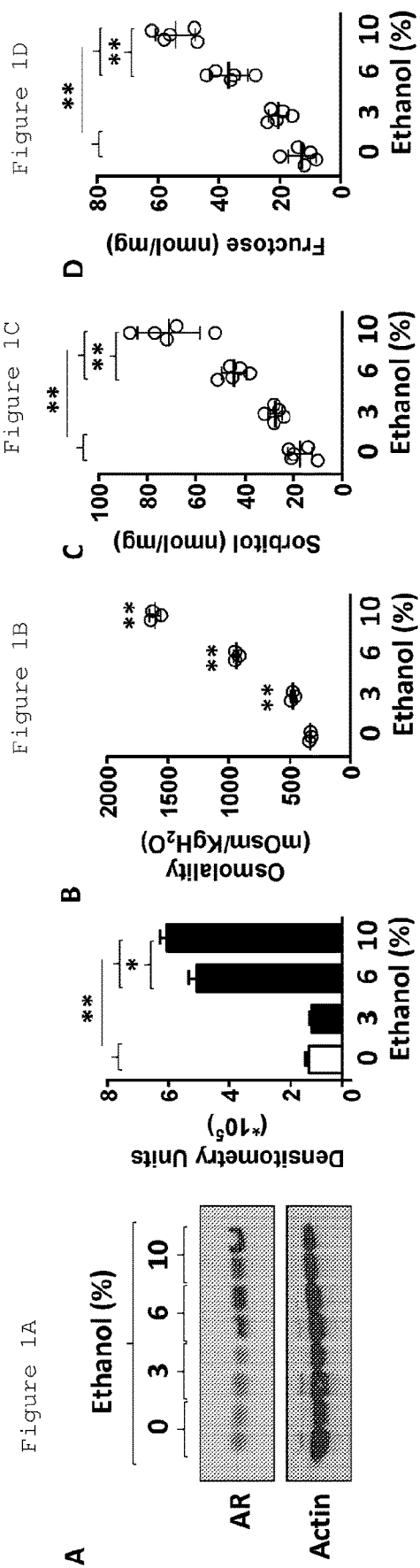

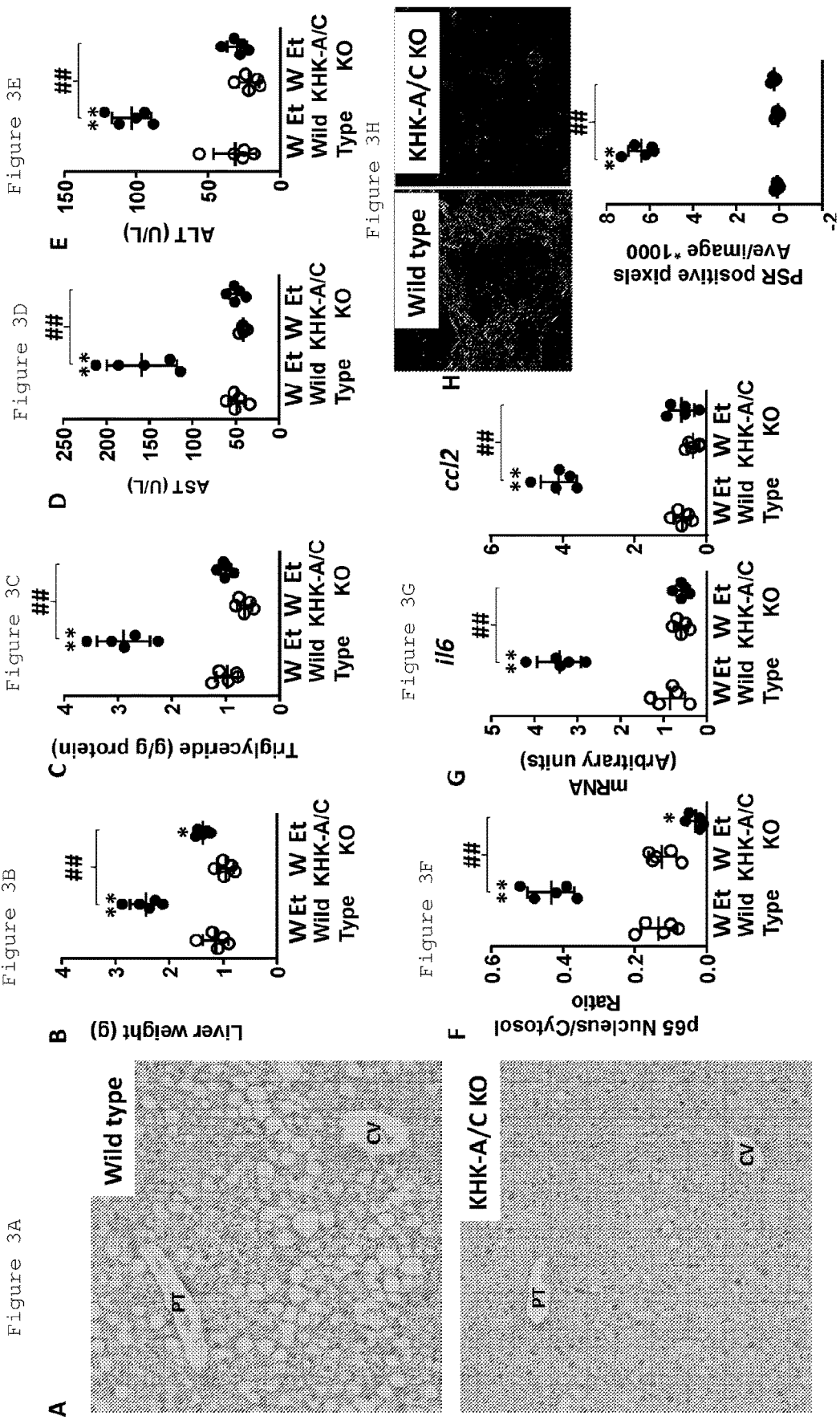

```
SEQUENCE LISTING

<160> NUMBER OF SEQ ID NOS: 1

<210> SEQ ID NO 1
<211> LENGTH: 298
<212> TYPE: PRT
<213> ORGANISM: Homo sapiens

<400> SEQUENCE: 1

Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30
```

-continued

```
Leu Ser Gln Arg Trp Gln Arg Gly Gly Asn Ala Ser Asn Ser Cys Thr
        35                  40                  45
Val Leu Ser Leu Leu Gly Ala Pro Cys Ala Phe Met Gly Ser Met Ala
        50                  55                  60
Pro Gly His Val Ala Asp Phe Leu Val Ala Asp Phe Arg Arg Arg Gly
65                      70                  75                  80
Val Asp Val Ser Gln Val Ala Trp Gln Ser Lys Gly Asp Thr Pro Ser
                85                  90                  95
Ser Cys Cys Ile Ile Asn Asn Ser Asn Gly Asn Arg Thr Ile Val Leu
                100                 105                 110
His Asp Thr Ser Leu Pro Asp Val Ser Ala Thr Asp Phe Glu Lys Val
            115                 120                 125
Asp Leu Thr Gln Phe Lys Trp Ile His Ile Glu Gly Arg Asn Ala Ser
        130                 135                 140
Glu Gln Val Lys Met Leu Gln Arg Ile Asp Ala His Asn Thr Arg Gln
145                 150                 155                 160
Pro Pro Glu Gln Lys Ile Arg Val Ser Val Glu Val Glu Lys Pro Arg
                165                 170                 175
Glu Glu Leu Phe Gln Leu Phe Gly Tyr Gly Asp Val Val Phe Val Ser
            180                 185                 190
Lys Asp Val Ala Lys His Leu Gly Phe Gln Ser Ala Glu Glu Ala Leu
        195                 200                 205
Arg Gly Leu Tyr Gly Arg Val Arg Lys Gly Ala Val Leu Val Cys Ala
        210                 215                 220
Trp Ala Glu Glu Gly Ala Asp Ala Leu Gly Pro Asp Gly Lys Leu Leu
225                 230                 235                 240
His Ser Asp Ala Phe Pro Pro Arg Val Val Asp Thr Leu Gly Ala
                245                 250                 255
Gly Asp Thr Phe Asn Ala Ser Val Ile Phe Ser Leu Ser Gln Gly Arg
                260                 265                 270
Ser Val Gln Glu Ala Leu Arg Phe Gly Cys Gln Val Ala Gly Lys Lys
            275                 280                 285
Cys Gly Leu Gln Gly Phe Asp Gly Ile Val
290                 295
```

METHODS FOR FRUCTOKINASE MEDIATION OF ALCOHOL CRAVING AND ALCOHOL INDUCED LIVER DISEASE

GOVERNMENT SUPPORT

This invention was made with government support under grants number NIDDK 1RO1DK108408-01A1 and NIDDK RO1DK108859-01 awarded by the National Institutes of Health. The government has certain rights in the invention.

BACKGROUND

Alcohol consumption is epidemic and can lead to multiple complications such as liver disease (cirrhosis), pancreatitis and dementia. The health costs of alcohol have been estimated to be 176 billion dollars/year in the United States alone. One of the reasons alcohol creates health problems is because it is addicting. Alcohol is known to directly affect numerous neurotransmitter systems in the brain, including serotonin, dopamine and glutamate pathways (1). Alcohol can also induce toxicity to various organs, especially the liver. Alcohol induces fatty liver, hepatitis, and over time, cirrhosis.(2) The mechanism is thought to be mediated by oxidative stress and glutathione depletion, abnormal methionine metabolism and toxic effects from ethanol breakdown products such as acetaldehyde.(2, 3) In essence, it is thought that alcohol or one of its byproducts is responsible for toxic effects to the liver and for its addicting properties.

Today the two most common sweeteners on the market are sugar (sucrose) and high fructose corn syrup (HFCS). Both sucrose and HFCS contain glucose and fructose, either as a disaccharide (sucrose) or as monomers (HFCS). Fructose is also present in fruits and honey. Sugar and HFCS can also stimulate dopamine and are thought to cause craving, and even possibly addiction, in some individuals. Sugar and its component fructose, for example, have been shown to stimulate dopamine, which results in a pleasure response.(4, 5) Indeed, Lustig has suggested that sugar or fructose intake is similar to alcohol (like "alcohol without the buzz").(6).(7)

Likewise, fructose has been found to also cause fatty liver disease in animals, and to be epidemiologically linked with fatty liver and steatohepatitis in humans with nonalcoholic fatty liver disease.(8) Fructose has also been found to potentiate alcohol in causing liver disease in animals (9). These authors concluded that fructose, through its own ability to cause liver disease, might lead to worse liver injury when given in combination with alcohol.

BRIEF DESCRIPTION OF THE DRAWINGS

FIGS. 1A-1D include results of a Western blot and densitometry graphs showing that alcohol consumption is associated with endogenous production of fructose in the liver. FIG. 1A provides Western blot and densitometry values for AR in the liver of mice exposed to 0%, 3%, 6%, and 10% alcohol for 10 weeks. FIG. 1B shows osmolality of water and 3%, 6% and 10% ethanol solutions. FIGS. 1C-1D provide results of intrahepatic sorbitol and fructose in the same mice as in FIG. 1A. $*p<0.05$ and $**p<0.01$ One Way ANOVA with Tukey post hoc analysis; n=5 mice per group.

FIG. 2A shows cumulative alcohol intake in wild type and fructokinase knockout (KHK-A/C KO) mice exposed to 10% alcohol for 30 weeks. FIG. 2B shows alcohol preference in two-bottle choice preference paradigms in wild type and fructokinase knockout (KHK-A/C KO) mice exposed to water and 3%, 6% and 10% alcohol solutions for 10 weeks. FIG. 2C provides delta FosB expression and densitometry in nucleus accumbens (Nacc) of wild type mice exposed to 0%, 3%, 6% and 10% alcohol for 10 weeks. FIG. 2D includes delta FosB expression and densitometry in nucleus accumbens (Nacc) of wild type and fructokinase knockout mice exposed to 10% alcohol for 10 weeks. FIG. 2E shows serum FGF21 levels in the same mice as in FIG. 2D.

FIGS. 3A-3H provide the results of blockade of fructokinase alcoholic liver disease. FIG. 3A provides Hematoxyline/eosine liver images in 10% alcohol wild type and 20% alcohol fructokinase knockout—to normalize for equal alcohol intake—for 30 weeks. FIGS. 3B-3E provide liver weight, triglycerides and serum transaminases (AST and ALT) in wild type water, 10% alcohol, fructokinase knockout water, and 20% alcohol exposed mice (30 weeks). FIGS. 3F-3G demonstrate the results of inflammation: nuclear expression of the pro-inflammatory transcription factor p65 and mRNA levels of its target genes il6 and ccl2 in the liver of wild type water, 10% alcohol, fructokinase knockout water and 20% alcohol exposed mice (30 weeks). FIG. 3H shows the results of fibrosis: Picro-Sirius red under polarized light images and total quantification in the liver of wild type water, 10% alcohol, fructokinase knockout water and 20% alcohol exposed mice (30 weeks) $*p<0.05$ and $**p<0.01$ versus respective controls $\#\#p<0.01$ One Way ANOVA with Tukey post hoc analysis; n=5 mice per group.

DETAILED DESCRIPTION

Figure 2A:
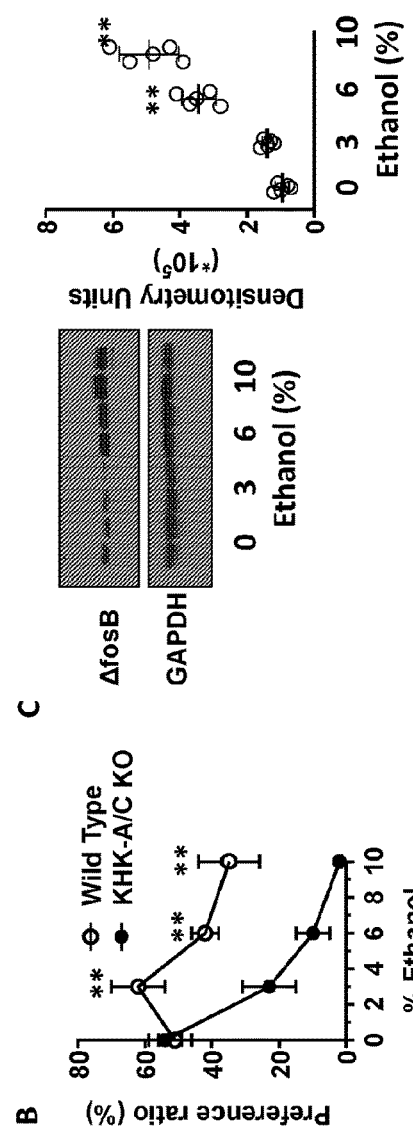
FIGS. 2A-2E demonstrate the blockade of fructokinase abrogates preference and intake of alcohol.
Figure 2B:
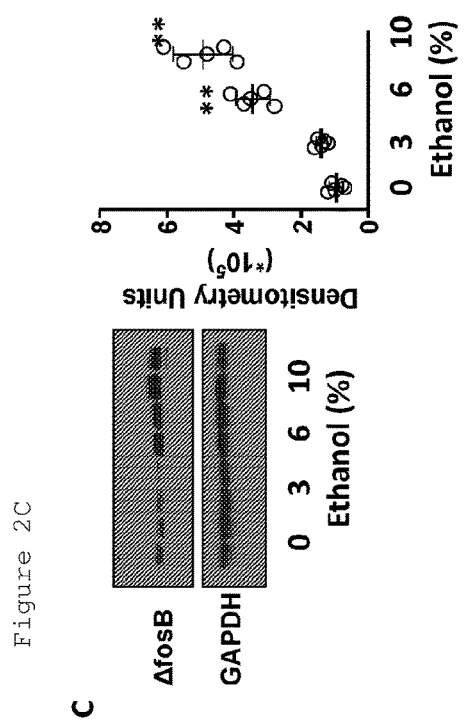

The recent studies described herein have identified effects of alcohol that were not previously noted in the literature. In one example, alcohol increases hepatic fructose levels. It is known that fructose causes sugar-induced liver disease. Similarly, alcohol causes alcohol-induced liver disease. Each form of liver disease caused by fructose or alcohol, however, involves a different metabolic pathway. The inventors have discovered herein that inhibition of fructose metabolism by inhibiting fructokinase can prevent the effects of alcohol to induce both addiction and prevent the effects of alcohol in causing alcohol-induced liver disease.

Overview

A key aspect of the aforementioned studies is that alcohol metabolism and fructose metabolism involve two separate, unrelated pathways. Alcohol is thought to cause addiction and liver disease as a result of alcohol metabolism. Fructose, by a separate metabolic pathway also causes addiction and liver disease. For the first time herein, it is discovered that alcohol stimulates fructose metabolism. It has been discovered herein that blocking sugar metabolism may prevent or treat alcohol addiction and alcohol-induced liver disease. Before the discoveries described herein, it was previously understood that each substance (i.e., alcohol, sugar) has effects on the liver and brain that are similar in effect, but distinct in mechanism.

Consequently, provided herein are methods for reducing an alcohol craving in a subject by inhibiting fructose metabolism. Additionally, methods for treating alcohol liver disease are provided by inhibiting fructose metabolism in a subject. In embodiments provided, inhibition of fructose metabolism, by for example, inhibiting fructokinase, can result in reducing or preventing a craving for alcohol in a subject, and furthermore, in preventing alcohol-induced liver disease. Liver disease is prevented or treated in a subject, even if the subject is exposed to alcohol. The inhibition of fructose metabolism by blocking fructokinase prevents liver toxicity.

The invention includes compositions and methods of treating or preventing an addictive disease or disorder. In one aspect, the invention includes a method of treating or preventing an addictive disease or disorder in a subject in need thereof comprising administering an effective amount of a KHK inhibitor.

In another aspect, the invention includes a method of decreasing alcohol consumption or craving in a subject in need thereof comprising administering an effective amount of a KHK inhibitor.

In yet another aspect, the invention includes a composition for treating or preventing an addictive disease or disorder, comprising an effective amount of a KHK inhibitor.

In still another aspect, the invention includes a composition for treating or preventing an addictive disease or disorder, comprising an effective amount of a KHK inhibitor, wherein the addictive disease or disorder is selected from the group consisting of alcoholism, alcohol dependence, or alcohol withdrawal, heavy alcohol consumption, excessive alcohol consumption, and combinations thereof.

In one embodiment, the addictive disease is alcoholism, alcohol dependence, or alcohol withdrawal. In such an embodiment, the step of administrating results in decreasing frequency of alcohol consumption. In another embodiment, the step of administrating results in decreasing alcohol consumption compared with before administration. In yet another embodiment, the step of administrating results in decreasing alcohol consumption and increasing abstinence of alcohol consumption.

In another embodiment, the step of administering the effective amount comprises administering about 0.05 mg to about 0.5 g per single dose, less than about 0.80 g daily, or within the range of about 0.001 mg/kg to about 100 mg/kg. In yet another embodiment, the step of administering comprises administration via an oral route.

In one embodiment, the composition further comprises a pharmaceutically acceptable carrier or adjuvant, such as including at least one binder, excipient, diluent, or any combinations thereof. In another embodiment, the composition is formulated for oral administration, such as a liquid suspension, a chewable composition, and an orally disintegrating tablet or capsule composition. In another embodiment, the composition is formulated for delayed-release.

In another embodiment, the effective amount comprises about 2 mg to about 100 mg per single dose. In yet another embodiment, the effective amount comprises less than about 50 mg daily.

Definitions

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the terms "disease," "disorder," or "complication" refers to any deviation from a normal state in a subject. In preferred embodiments, the methods and compositions of the present invention are useful in the treatment of diseases where the expression or activity of a KHK contributes to the disease, or related to fructose intake or metabolism, or where the presence of KHK is correlated with a positive indication of the disease in a subject. The present invention finds use with any number of diseases including, but not limited to liver diseases, pancreatic conditions, and related health complications.

As used herein, the term "liver disease" includes, but is not limited to fatty liver, steatohepatitis and cirrhosis.

As used herein, by the term "effective amount," "amount effective," "therapeutically effective amount," or the like, it is meant an amount effective at dosages and for periods of time necessary to achieve the desired result.

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "expression" in the context of a gene or polynucleotide involves the transcription of the gene or polynucleotide into RNA. The term may also, but not necessarily, involve the subsequent translation of the RNA into polypeptide chains and their assembly into proteins.

As used herein, the term "KHK inhibitor" includes an inhibitor that selectively inhibits ketohexokinase activity and/or expression of KHK. In a specific embodiment, the KHK inhibitor inhibits KHK-C or both KHK-A and KHK-C.

As used herein, the terms "KHK", "ketohexokinase", and "fructokinase" are used interchangeably herein and refers to an enzyme that catalyzes the phosphorylation of fructose to produce fructose-1-phosphate. Human KHK includes various isozymes such as KHK-C or KHK-A. One example of a cDNA sequence that encodes human KHK is provided as Accession No. CR456801. One example of an amino acid sequence pertaining to a human KHK enzyme is Accession No. CAG33082. Other examples of KHK sequences include NM_006488 (KHK-C isoform) or NM_000221 (KHK-A isoform). An amino acid sequence of human KHK-C is provided below SEQ ID NO. 1:

```
          10         20         30         40
    MEEKQILCVG LVVLDVISLV DKYPKEDSEI RCLSQRWQRG 50         60         70         80
    GNASNSCTVL SLLGAPCAFM GSMAPGHVAD FLVADFRRRG 90        100        110        120
    VDVSQVAWQS KGDTPSSCCI INNSNGNRTI VLHDTSLPDV
```

```
            130        140        150        160
      SATDFEKVDL TQFKWIHIEG RNASEQVKML QRIDAHNTRQ 170        180        190        200
      PPEQKIRVSV EVEKPREELF QLFGYGDVVF VSKDVAKHLG 210        220        230        240
      FQSAEEALRG LYGRVRKGAV LVCAWAEEGA DALGPDGKLL 250        260        270        280
      HSDAFPPPRV VDTLGAGDTF NASVIFSLSQ GRSVQEALRF

290
      GCQVAGKKCG LQGFDGIV
```

Interfering molecules may be designed against a portion of KHK sequence that encodes SEQ ID NO. 1 above.

As used herein, the terms "interfering molecule" refer to all molecules that have a direct or indirect influence on gene expression, such as the silencing of a target gene sequence. Interfering molecules include inhibitory oligonucleotides, RNA interfering molecules and RNA-like interfering molecules. Examples of interfering RNA molecules include antisense sequences, siRNAs, short hairpin RNAs (shRNAs), single-stranded siRNAs, microRNAs (miRNAs), methylated siRNAs or other siRNAs treated to protect the siRNA from degradation by circulating RNases, and dicer-substrate 27-mer duplexes. Examples of "RNA-like" molecules include, but are not limited to, siRNA, single-stranded siRNA, microRNA, and shRNA molecules that contain one or more chemically modified nucleotides, one or more non-nucleotides, one or more deoxyribonucleotides, and one or more non-phosphodiester linkages. Thus, siRNAs, single-stranded siRNAs, shRNAs, miRNAs, and dicer-substrate 27-mer duplexes are subsets of "interfering molecules." "Interfering molecules" also may include PMOs.

As used herein, the terms "phosphothioate morpholino oligomer(s)," "a PMO" or "PMOs" refer to molecules having the same nucleic acid bases naturally found in RNA or DNA (i.e. adenine, cytosine, guanine, uracil or thymine), however, they are bound to morpholine rings instead of the ribose rings used by RNA. They may also linked through phosphorodiamidate rather than phosphodiester or phosphorothioate groups. This linkage modification eliminates ionization in the usual physiological pH range, so PMOs in organisms or cells are uncharged molecules. The entire backbone of a PMO is made from these modified subunits.

As used herein, the term "antisense sequence" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these.

The term "inhibitory oligonucleotide" refers to any oligonucleotide that reduces the production or expression of proteins, such as by interfering with translating mRNA into proteins in a ribosome or that are sufficiently complementary to either a gene or an mRNA encoding one or more targeted proteins, that specifically bind to (hybridize with) the one or more targeted genes or mRNA thereby reducing expression or biological activity of the target protein. Inhibitory oligonucleotides include isolated or synthetic shRNA or DNA, siRNA or DNA, antisense RNA or DNA, Chimeric Antisense DNA or RNA, miRNA, and miRNA mimics, among others.

As used herein, "siRNAs" (short interfering RNAs), also known as small interfering RNA or silencing RNA refer to double-stranded RNA molecules, generally around 15-30 nucleotides in length, that are complementary to the sequence of the mRNA molecule transcribed from a target gene, and interferes with the expression of the target gene.

As used herein, "shRNAs" (small hairpin RNAs) are short "hairpin-turned" RNA sequences that may be used to inhibit or suppress gene expression.

As used herein, a "composition," "pharmaceutical composition" or "therapeutic agent" all include a composition comprising at least a KHK inhibitor. Optionally, the "composition," "pharmaceutical composition" or "therapeutic agent" further comprises pharmaceutically acceptable diluents or carriers, and/or a conjunctive agent. In the case of an interfering molecule, for example, the interfering molecule may be combined with one or more pharmaceutically acceptable diluents, such as phosphate-buffered saline, for example. As used herein, a pharmaceutical composition particularly refers to a composition comprising at least a KHK inhibitor that is intended to be administered to a subject as described herein.

The term micro RNA (abbreviated miRNA) is a small non-coding RNA molecule (containing about 22 nucleotides) found in plants, animals and some viruses, that functions in RNA silencing and post-transcriptional regulation of gene expression. The miRNAs resemble the small interfering RNAs (siRNAs) of the RNA interference (RNAi) pathway, except miRNAs derive from regions of RNA transcripts that fold back on themselves to form short hairpins, whereas siRNAs derive from longer regions of double-stranded RNA. Under a standard nomenclature system, names are assigned to experimentally confirmed miRNAs. The prefix "miR" is followed by a dash and a number, the latter often indicating order of naming. "MIR" refers to the gene that encodes a corresponding miRNA. Different miRNAs with nearly identical sequences except for one or two nucleotides are annotated with an additional lower case letter. The term miRNA mimics, refers to small, double-stranded RNA molecules, such as siRNA, designed to mimic endogenous mature miRNA molecules when introduced into cells.

Compounds and compositions for inhibiting KHK activity specifically may include one or more compounds that may function as active ingredients. The compound may be a component of a plant extract. For example, the compound may include a phytochemical present in the plant from which the plant extract is obtained. The compound may be at least partially responsible for the inhibition of KHK activity exhibited by the plant extract. The compound may include any compound capable of inhibiting KHK-activity, such as a small molecule described below. In other examples, the KHK inhibitor may be a peptide or a KHK-specific antibody.

As used herein, the term "prevent", "prevention" or "preventing" means causing the clinical symptoms of the disease state not to develop, e.g., inhibiting the onset of disease, in a subject that may be exposed to or predisposed to the disease state, but does not yet experience or display symptoms of the disease state. The terms as used herein may further include either 1) the reduction in frequency or severity of symptoms commonly associated with the disorder; or 2) a delay or avoidance of additional symptoms associated with the condition or disease, or complete prevention of the disease. One skilled in the art will recognize that wherein the various embodiments are directed to methods of prevention, a subject in need thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

In the case of the co-administration of a KHK inhibitor with a conjunctive agent as described herein, the conjunctive agent, the KHK inhibitor, or the combination of the KHK inhibitor and the conjunctive agent may supply the effective amount.

As used herein, the term "subject" refers to any animal (e.g., a mammal), including, but not limited to, humans, non-human primates, rodents, and the like, which is to be the recipient of a particular treatment.

As used herein, the terms "treat" "treating", "treatment" or "alleviation" refers to therapeutic treatment, wherein the object is to halt, slow down or reverse a pathological condition or disorder In one example, the terms may further include administering a compound to manage the symptoms or underlying cause of a condition with the goal of reducing symptoms or signs of the disease and either to prevent or to slow progression, to arrest or potentially to reverse manifestations of the disease, or to inhibit the underlying mechanism(s) causing the disease. For example, treating alcohol addiction comprises the amelioration, reduction or cessation of the desire for and habit of consuming alcoholic drinks, the treatment of alcohol dependence and the treatment of abstinence syndrome. In an alternative example, treatment involves administering a KHK inhibitor to a person who is admitted for diseases related to alcohol, such as alcohol pancreatitis, alcohol addiction and or withdrawal, or alcohol induced liver disease (such as acute alcoholic hepatitis or alcoholic cirrhosis) to reduce progression and or recurrence or readmission for these various conditions.

As used herein, the terms "crave" or "craving" refers to a desire for ingestion or consumption of a substance (e.g. alcohol).

By "addictive disease" or "addiction" is meant a primary or chronic disease of brain reward, motivation, memory and related circuitry. Dysfunction in these circuits leads to characteristic biological, psychological, social and spiritual manifestations. This is reflected in an individual pathologically pursuing reward and/or relief by substance use and other behaviors. Addiction is characterized by inability to consistently abstain, impairment in behavioral control, craving, diminished recognition of significant problems with a subject's behaviors and interpersonal relationships, and a dysfunctional emotional response. Like other chronic diseases, addiction often involves cycles of relapse and remission. Without treatment or engagement in recovery activities, addiction is progressive and can result in disability or premature death. Examples of addictive diseases or disorders include, but are not limited to, alcohol or drug abuse.

The term "alcoholism" according to the invention includes alcohol abuse, alcohol dependence and other problems with alcohol, and is generally used to mean compulsive and uncontrolled consumption of alcoholic beverages, usually to the detriment of the drinker's health, personal relationships, and social standing. It is a chronic disease, specifically an addictive illness. The term "alcohol abuse" is defined in the Diagnostic and Statistical Manual of Mental Disorders (DSM-IV). Alcohol abuse is a maladaptive pattern of alcohol use that leads to clinically significant impairment or distress. Symptoms include one or more of the following occurring within a 12-month period: recurrent alcohol use that results in a failure to fulfill major role obligations at work, school or home; recurrent alcohol use in physically hazardous situations; recurrent alcohol-related legal problems; and continued alcohol use despite having persistent or recurrent social or interpersonal problems caused or exacerbated by the effects of the substance By "alcohol dependence" is meant symptoms of alcohol abuse accompanied by one or more of the following: alcohol tolerance; withdrawal manifested by characteristic withdrawal syndrome for alcohol or alcohol taken to relieve or avoid withdrawal symptoms; alcohol taken in larger amounts over a longer period than as intended; a persistent desire or unsuccessful efforts to reduce or control drinking; much time spent in activities necessary to obtain alcohol, use alcohol, or recover from its effects; important social, occupational, or recreational activities being given up or reduced because of drinking; and continued use despite knowledge of having a persistent or recurrent physical or psychological problem caused or exacerbated by alcohol.

By "alcohol tolerance" is meant a need for markedly increased amounts of alcohol to achieve intoxication or desired effect or a markedly diminished effect of alcohol with continued use of the same amount of alcohol.

"Alcohol withdrawal" means the symptoms associated with cessation of alcohol intake. With repeated heavy consumption of alcohol, gamma-aminobutyric acid (GABA) receptors are desensitized and reduced in number, resulting in tolerance and physical dependence. When alcohol consumption is stopped too abruptly, the person's nervous system suffers from uncontrolled synapse firing. This can result in symptoms that include anxiety, life threatening seizures, delirium tremens, hallucinations, shakes and possible heart failure.

As used herein, the term "reducing" refers to diminishing the amount or level by at least 5%. In the context of KHK, reducing refers to lowering levels of expression and/or activity of KHK.

Conjunctive Therapeutic Agents

In any of the composition or method embodiments described herein, any of the exemplary therapeutic agents can be co-administered with other appropriate agents (conjunctive agent or conjunctive therapeutic agent) for the treatment or prevention of a target disease. Selection of the appropriate conjunctive agents for use in combination therapy can be made by one of ordinary skill in the art, according to conventional pharmaceutical principles. The combination of therapeutic agents can act synergistically or additively to affect the treatment or prevention of the various disorders described above. Using this approach, one may be able to achieve therapeutic efficacy with lower dosages of each agent, thus reducing the potential for adverse side effects. Any of the therapeutic methods and compositions comprising an exemplary therapeutic agent described herein can be co-administered with another conjunctive agent to a subject in need of such therapy.

Exemplary conjunctive agents that may be formulated or administered with any form of an exemplary therapeutic agent as described herein include one or more of the KHK inhibitors described herein.

Examples of conjunctive agents which may be used herein include one or more aldose reductase agents, uric acid lowering agents, corticosteroid (e.g. prednisone), pentoxifylline, or steroid derivatives. The aldose reductase agents may include sorbanil, zopolrestat, ponalrestat, or toirestat. The uric acid lowering agents may include allopurinol, oxypurinol, febuxostat, lesinurad, or verinurad. Other conjunctive agents include naltrexone, acamprosate, baclofen, disulfiram, Antabuse, campral, and lioresal, or some combination thereof.

As used herein, the terms "co-administered, "co-administering," or "concurrent administration" when used, for example with respect to administration of an exemplary therapeutic agent with another exemplary therapeutic agent, or a conjunctive agent along with administration of an exemplary therapeutic agent refers to administration of the exemplary therapeutic agent and the other exemplary therapeutic agent or conjunctive agent such that both can simultaneously achieve a physiological effect. The two agents, however, need not be administered together. In certain embodiments, administration of one agent can precede administration of the other, however, such co-administering typically results in both agents being simultaneously present in the body (e.g. in the plasma) of the subject.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

KHK Inhibitors

According to certain embodiments, KHK inhibitors are administered to a subject in need. Provided below is a discussion of known KHK inhibitors that can be implemented for this purpose.

Small Molecules

Small Molecules which may be used as a KHK inhibitor as disclosed herein, may include, for example, Osthol, Cratoxyarborenone E, Mangostin (e.g. gamma-Mangostin or alpha-Mangostin), Osthenol, a Polyketide type molecule, 4-Hydroxy-Derricin, Isobavachalcone, Methoxy isobavachalcone, Oroxylin A, 5,7-Dimethoxy-8-prenylcoumarin, Apigenin 7-glucuronide, 3',4',5,7-THMethoxy3'-O-β-D-Xylopyranoside, Swietenocoumarin B, Apiin, Mulberrin, Flavaspidic acid AB, Phloretin, an indazole, a pyrimidinopyrimidine, luteolin, (Z)-3-(methylthio)-1-phenyl-N'-(((4-(trifluoromethoxy)phenyl)carbamoyl)oxy)-1H-pyrazole-4-carboximidamide; 5-amino-3-(methylthio)-1-phenyl-1H-pyrazole-4-carbonitrile; 2-(3-(methylthio)-1-phenyl-1H-pyrazol-4-yl)-4-phenylthiazole; or combinations thereof.

Other small molecule KHK inhibitors are found in US Patent Pubs 2011/0263559 and 2017/0183328; U.S. Pat. No. 8,822,447; PCT App No. PCT/US18/23186; *J. Med. Chem.* 2010, 53, 7979-799; *J Med Chem.* 2017 Sep. 28; 60(18): 7835-7849; *Bioorg Med Chem Lett.* 2012 Aug. 15; 22(16): 5326-9; *Bioorg Med Chem Lett.* 2011 Aug. 15; 21(16):4762-7; *J Clin Invest.* 2017 Nov. 1; 127(11):4059-4074; Optimization of the chemical matter and synthesis leading to a ketohexokinase inhibitor clinical candidate, Division of Medicinal Chemistry Scientific Abstracts 255th National meeting and Exposition, 2018, New Orleans, LA.

Other small molecule KHK inhibitors that may be used in accord with methods taught herein are Indozole based inhibitors as taught in PCT Pub No. WO2018/170571 (Regents of the University of Colorado). In particular, the indozole inhibitors are represented by Formula I below:

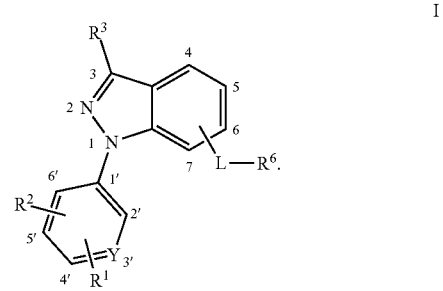

Referring to Formula I, $R^1$, $R^2$ may be independently selected from: —H, D, —$C_1$-$C_5$-straight chain alkyl, —$C_1$-$C_5$-branched alkyl, —$C_3$-$C_5$-cycloalkyl, —$(CH_2)_n$—$C_3$-$C_5$-cycloalkyl, —NH—$(CH_2)_n$—$C_3$-$C_5$-cycloalkyl —F, —Cl, —Br, —$CF_3$, —$CHF_2$, —$OCF_3$, —$OCHF_2$, —O—$C_3$-$C_5$-cycloalkyl, —O—$C_3$-$C_5$-alkyl, —CN, —$SO_2$—$C_1$-$C_4$-alkyl, —$SO_2CF_3$, —$SO_2$—$C_1$-$C_4$-cycloalkyl, —$Si(CH_3)_3$, —C≡C—$C_1$-$C_4$-alkyl, —C≡C—$C_3$-$C_5$-cycloalkyl; $COOR^5$, $CON(R^5)_2$, and $SO_2N(R^5)_2$, wherein n may be from 1-4.

Still referring to Formula I, $R^3$ may be selected from: —H, -cyclopropyl, -cyclobutyl, —$CH_2OCH_3$, 3-oxetanyl, —O—$C_3$-$C_5$-cycloalkyl, —$C(R_5)_2O$—$C_1$-$C_4$-alkyl, and —$CH_2O$—$C_3$-$C_5$-cycloalkyl.

Still referring to Formula I, L may represent simply a covalent bond to an $R^6$ group, as described below, or to a moiety selected from: —O—, —$NR^5$—, —$CONR^5$—, —$NR^5CO$—, —O—$[C(R^5)_2]_n$—, —$CH_2OCH_2$—, —[C$(R^5)_2]_n$—O—, —CO—, —$[C(R^5)_2]_n$—, —$CR^5(OH)$—, —$[C(R^5)_2]_n$—$NR^5$—, —$SO_2N(R^5)$—, —$SO_2$—, and —N—$[C(R^5)_2]_n$, wherein n may be from 1-4. $R^5$ may be selected independently from: —H, and a $C_1$-$C_5$-alkyl.

Still referring to Formula I, $R^6$ may be selected from: —$(CH_2)_n$—$N(R^5)_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, indol-5-yl, each of which may be substituted with from 1 to 3 $R^4$ substituents, which may be selected from $C_1$-$C_5$-alkyl, $C_3$-$C_7$-cycloalkyl, —$N(R^5)_2$, —Cl, —F, —Br, —$OR^5$, —O—$C_3$-$C_7$-cycloalkyl, —CN, —$CF_3$, —$CHF_2$, —$OCF_3$, —$OCHF_2$, except where such substitution would be expected to yield unstable compounds. n may be from 1-4.

Still referring to Formula I, when L is selected from —CO, —$O(CH_2)_2$—, —$(CH_2)_n$, $R^6$ may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

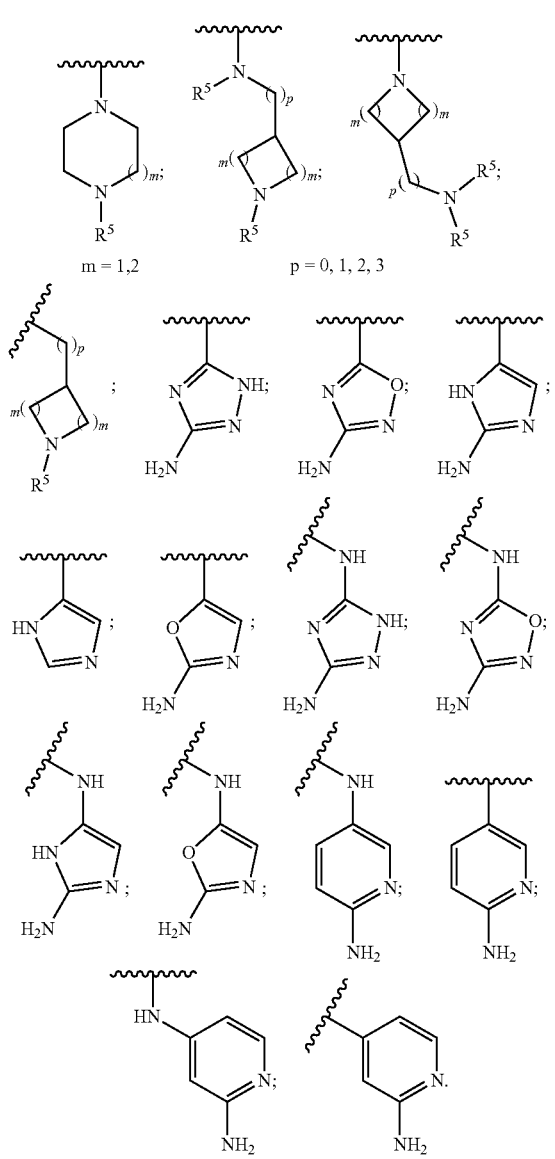

Finally, still referring to Formula I, Y may be selected from N and CH.

Further embodiments relate to compounds as set forth in Formula II below:

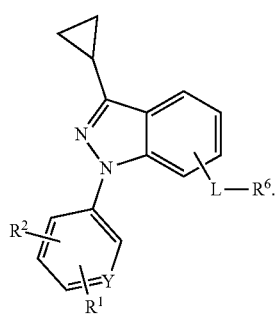

II

As shown in Formula II, $R^1$ may be selected from: —H, —$C_1$-$C_5$-alkyl, —$C_3$-$C_5$-cycloalkyl, —$(CH_2)_n$-$C_3$-$C_5$-cycloalkyl, —F, —Cl, —Br, —$CF_3$, —$CHF_2$, —$OCF_3$, —$OCHF_2$, —O—$C_3$-$C_8$-cycloalkyl, —CN, —$SO_2$—$C_1$-$C_4$-alkyl, —$SO_2CF_3$, —$SO_2$—$C_1$-$C_4$-cycloalkyl, —Si$(CH_3)_3$, —C≡C—$C_1$-$C_4$-alkyl, and —C≡C—$C_3$-$C_5$-cycloalkyl, wherein n may be from 1 to 4.

Still referring to Formula II, R2 may be selected from: —H, —$C_1$-$C_5$-alkyl, —$C_3$-$C_5$-cycloalkyl, —$(CH_2)_n$-$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —Si$(CH_3)_3$, —C≡C—$C_1$-$C_4$-alkyl, and —C≡C—$C_3$-$C_5$-cycloalkyl, wherein n may be from 1 to 4.

Still referring to Formula II, L may represent simply a covalent bond to an $R^6$ group, as described below, or to a moiety selected from: —O—, —$CONR^5$—, O—CH($R^5$)—, —$CH_2OCH_2$—, —CH($R^5$)—O—, —$O(CH_2)_2$—, —CO—, —$(CH_2)_n$—, and —CH(OH)—, wherein $R^5$ may be selected from: —H, and $C_1$-$C_5$-alkyl, and, wherein n may be from 1 to 4.

Still referring to Formula II, $R^6$ may be selected from: —$(CH_2)_n$-N$(R^5)_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, and indol-5-yl, each of which may be substituted with from 1 to 3 $R^4$ substituents, which may be selected from: $C_1$-$C_5$-alkyl, $C_1$-$C_5$-cycloalkyl, —N($R^5$) 2, —Cl, —F, —Br, —$OR^5$, —O-cyclopropyl, —CN, —$CF_3$, —$CHF_2$, —$OCF_3$, and —$OCHF_2$, except where such substitution would be expected to yield unstable compounds. n may be from 1-4.

Still referring to Formula II, when L is selected from —CO, —$O(CH_2)_2$—, and —$(CH_2)_n$, $R^6$ may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

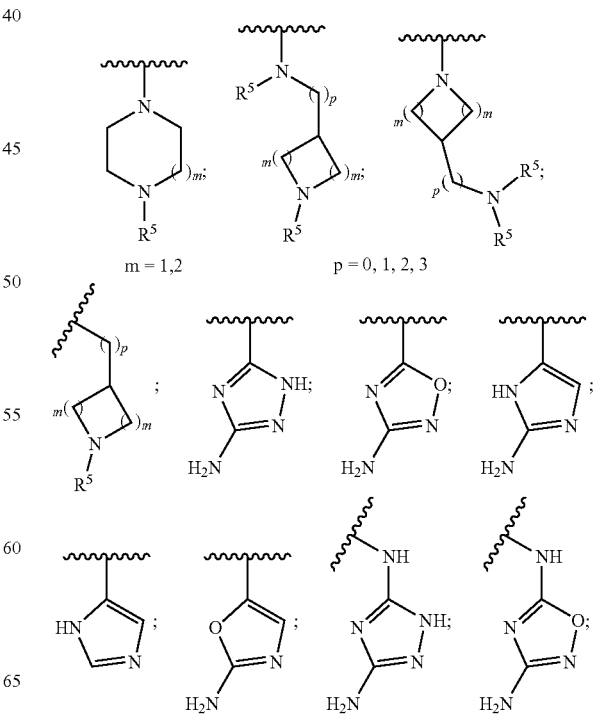

-continued

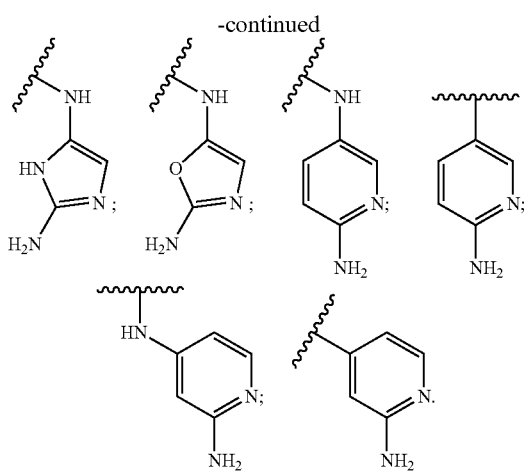

Finally, still referring to Formula II, Y may be selected from N and CH.

Other embodiments pertain to compounds set forth in Formula III below:

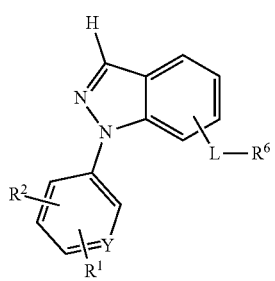

III

As shown in Formula III, $R^1$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —Si$(CH_3)_3$, —C≡C—$C_1$-$C_4$-alkyl, and —C≡C—$C_3$-$C_5$-cycloalkyl, wherein n may be from 1 to 4.

Still referring to Formula III, $R^2$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —Si$(CH_3)_3$, —C≡C—$C_1$-$C_4$-alkyl, and —C≡C—$C_3$-$C_5$-cycloalkyl, wherein n may be from 1 to 4.

Still referring to Formula III, L may represent simply a covalent bond to an $R^6$ group, as described below, or to a moiety selected from: —O—, —$CONR^5$—, O—CH($R^5$)—, —$CH_2OCH_2$—, —CH($R^5$)—O—, —O$(CH_2)_2$—, —CO—, —$(CH_2)_n$—, and —CH(OH)—, wherein $R^5$ may be selected from: —H, and $C_1$-$C_5$-alkyl, and, wherein n may be from 1 to 4.

Still referring to Formula III, $R^6$ may be selected from: —$(CH_2)_n$—N$(R^5)_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, indol-5-yl, each of which may be substituted with one to three $R^4$ substituents, which may be selected from: $C_1$-$C_5$-alkyl, $C_1$-$C_5$-cycloalkyl, —N$(R^5)_2$, —Cl, —F, —Br, —$OR^5$, —O-cyclopropyl, —CN, —$CF_3$, —$CHF_2$, —$OCF_3$, and —$OCHF_2$, except where such substitution would be expected to yield unstable compounds. n may be from 1-4.

Still referring to Formula III, when L is selected from —CO, —O$(CH_2)_2$—, and —$(CH_2)_n$, $R^6$ may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

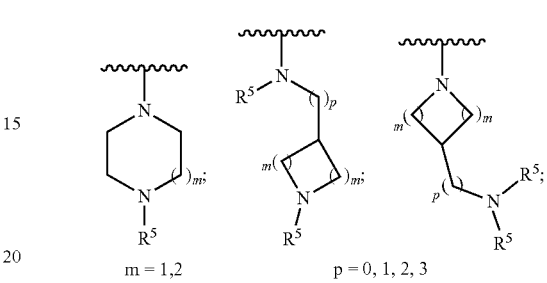

m = 1,2       p = 0, 1, 2, 3

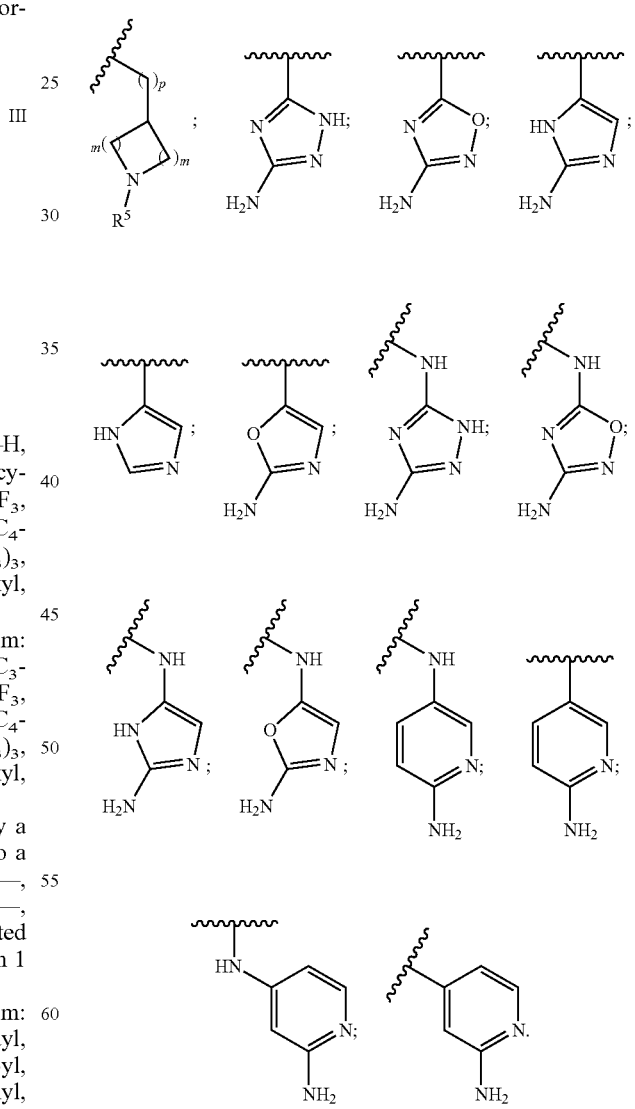

Finally, still referring to Formula III, Y may be selected from N and CH.

Various embodiments pertain to compounds as set forth in Formula IV below:

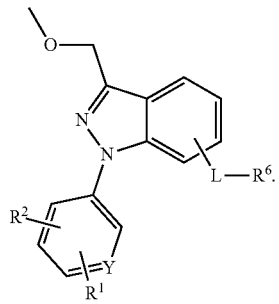

Referring to Formula IV, $R^1$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —$Si(CH_3)_3$, —C≡C—$C_1$-$C_4$-alkyl, and —C≡C—$C_3$-$C_5$-cycloalkyl, wherein n may be from 1 to 4.

Still referring to Formula IV, $R^2$ may be selected from: —H, —$C_1$-$C_5$-alkyl, —$C_3$-$C_5$-cycloalkyl, —$(CH_2)_n$—$C_3$-$C_5$-cycloalkyl, —F, —Cl, —Br, —$CF_3$, —$CHF_2$, —$OCF_3$, —$OCHF_2$, —O—$C_3$-$C_5$-cycloalkyl, —CN, —$SO_2$—$C_1$-$C_4$-alkyl, —$SO_2CF_3$, —$SO_2$—$C_1$-$C_4$-cycloalkyl, —$Si(CH_3)_3$, —C≡C—$C_1$-$C_4$-alkyl, and —C≡C—$C_3$-$C_5$-cycloalkyl, wherein n may be from 1 to 4.

Still referring to Formula IV, L may represent simply a covalent bond to an $R^6$ group, as described below, or to a moiety selected from: —O—, —$CONR^5$—, O—$CH(R^5)$—, —$CH_2OCH_2$—, —$CH(R^5)$—O—, —$O(CH_2)_2$—, —CO—, —$(CH_2)_n$—, and —CH(OH)—, wherein $R^5$ may be selected from: —H, and $C_1$-$C_5$-alkyl, and, wherein n may be from 1 to 4.

Still referring to Formula IV, $R^6$ may be selected from: —$(CH_2)_n$—$N(R^5)_2$, 2-pyridyl, 3-pyridyl, 4-pyridyl, 3-pyridazinyl, 4-pyridazinyl, 1-piperazinyl, pyrimidin-2-yl, pyrimidin-4-yl, pyrimidin-5-yl, 4-piperidinyl, 3-piperidinyl, 3-azetidinyl, 3-pyrolidinyl, 3-imidazolyl, 4-imidazolyl, 1,2,4-oxadiazol-5-yl, 1,2,4-triazol-3-yl, benzimidazol-5-yl, and indol-5-yl, each of which may be substituted with one to three $R^4$ substituents, which may be selected from: $C_1$-$C_5$-alkyl, $C_1$-$C_5$-cycloalkyl, —$N(R^5)_2$, —Cl, —F, —Br, —$OR^5$, —O-cyclopropyl, —CN, —$CF_3$, —$CHF_2$, —$OCF_3$, and —$OCHF_2$, except where such substitution would be expected to yield unstable compounds. n may be from 1-4.

Still referring to Formula IV, when L is selected from —CO, —$O(CH_2)_2$—, and —$(CH_2)_n$, $R^6$ may be selected from: 2-azaspiro[3.3]heptan-6-yl, octahydropyrrolo[3,4-c]pyrrol-1-yl, 1-piperazinyl, 2,6-diazaspiro[3.3]heptan-1-yl,

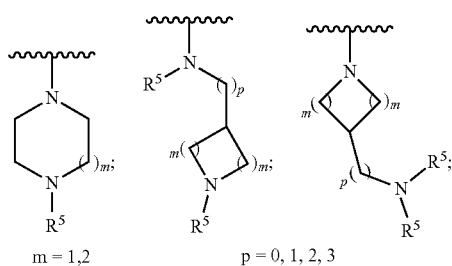

m = 1,2      p = 0, 1, 2, 3

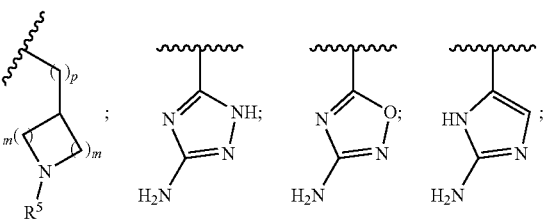

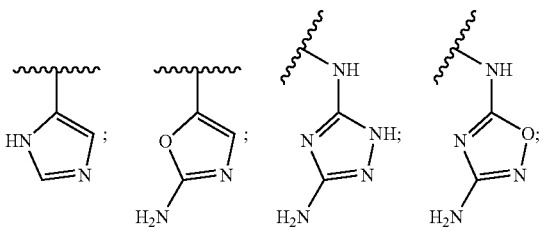

Finally, still referring to Formula IV, Y may be selected from N and CH.

The exemplary therapeutic agents described above are fructokinase inhibitors that may be administered to treat or prevent metabolic disorders and diseases. Furthermore, some of the crystalline forms for the compounds according to various embodiments may exist as polymorphs and as such are intended to be included in the within the scope of this disclosure. In addition, some of the compounds according to various embodiments may form solvates with water (i.e., hydrates) or common organic solvents, and such solvates are also intended to be encompassed within the scope of this disclosure.

Table 1 provides a list of specific species of exemplary therapeutic agents. Table 1 includes the IUPAC Name for each compound as well as a mass-to-charge ratio (m/z) for each compound. As used herein, the term "mass-to-charge ratio" refers to a dimensionless quantity formed by dividing the ratio of the mass of an ion to the unified atomic mass unit, by its charge number (regardless of sign).

TABLE 1

| Compound | TEMP SPR CROSS REF | Structure | IUPAC Name | M/Z |
|---|---|---|---|---|
| C-1 | SPR439 | 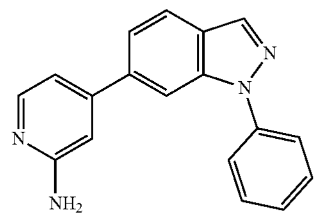 [SMILES: Nc1cc(-c2ccc3cnn(-c4ccccc4)c3c2)ccn1] | 4-(1-phenyl-1H-indazol-6-yl)pyridin-2-amine | 287 |
| C-2 | SPR306 | 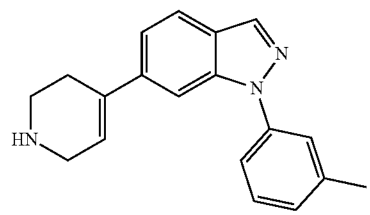 [SMILES: Cc1cccc(-n2ncc3ccc(C4=CCNCC4)cc32)c1] | 6-(1,2,3,6-tetrahydropyridin-4-yl)-1-(m-tolyl)-1H-indazole | 290 |
| C-3 | SPR356 | 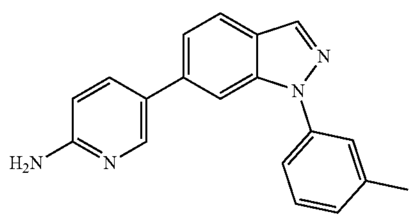 [SMILES: Cc1cccc(-n2ncc3ccc(-c4ccc(N)nc4)cc32)c1] | 5-(1-(m-tolyl)-1H-indazol-6-yl)pyridin-2-amine | 301 |
| C-4 | SPR361 | 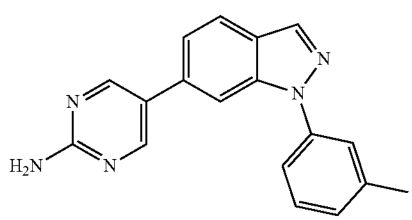 [SMILES: Cc1cccc(-n2ncc3ccc(-c4cnc(N)nc4)cc32)c1] | 5-(1-(m-tolyl)-1H-indazol-6-yl)pyrimidin-2-amine | 302 |
| C-5 | SPR366 | 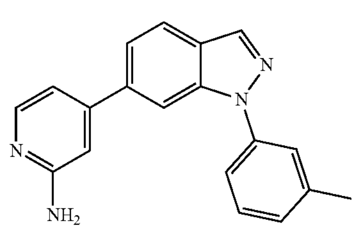 [SMILES: Cc1cccc(-n2ncc3ccc(-c4ccnc(N)c4)cc32)c1] | 4-(1-(m-tolyl)-1H-indazol-6-yl)pyridin-2-amine | 301 |
| C-6 | SPR326 | 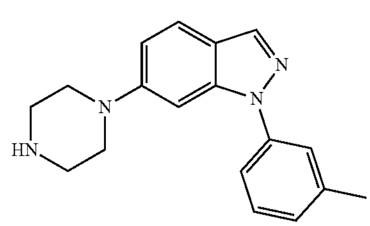 | 6-(piperazin-1-yl)-1-(m-tolyl)-1H-indazole | 293 |

TABLE 1-continued

| Compound | TEMP SPR CROSS REF | Structure | IUPAC Name | M/Z |
|---|---|---|---|---|
| C-7 | SPR360 | 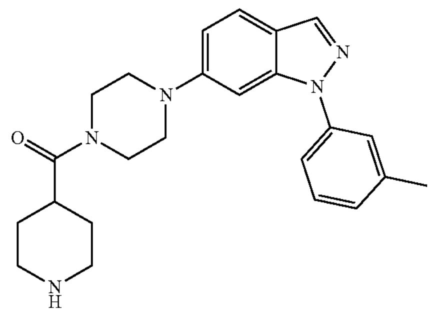 [SMILES: Cc1cccc(-n2ncc3ccc(N4CCN(C(=O)C5CCNCC5)CC4)cc32)c1] | piperidin-4-yl(4-(1-(m-tolyl)-1H-indazol-6-yl)piperazin-1-yl)methanone | 404 |
| C-8 | SPR329 | 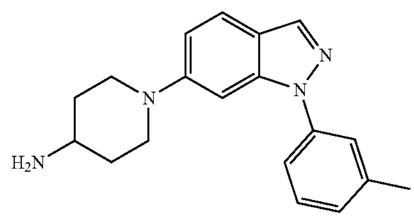 [SMILES: Cc1cccc(-n2ncc3ccc(N4CCC(N)CC4)cc32)c1] | 1-(1-(m-tolyl)-1H-indazol-6-yl)piperidin-4-amine | 307 |
| C-9 | SPR339 | 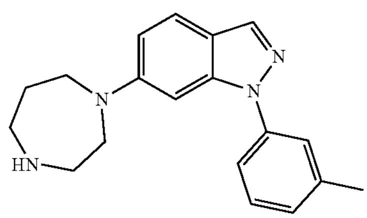 [SMILES: Cc1cccc(-n2ncc3ccc(N4CCCNCC4)cc32)c1] | 6-(1,4-diazepan-1-yl)-1-(m-tolyl)-1H-indazole | 307 |
| C-10 | SPR353 | 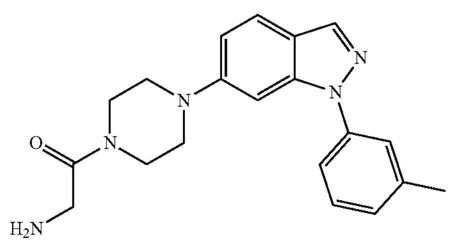 [SMILES: Cc1cccc(-n2ncc3ccc(N4CCN(C(=O)CN)CC4)cc32)c1] | 2-amino-1-(4-(1-(m-tolyl)-1H-indazol-6-yl)piperazin-1-yl)ethan-1-one | 350 |
| C-11 | SPR359 | 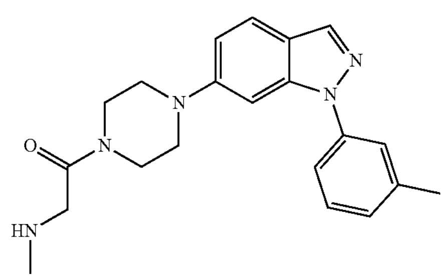 [SMILES: CNCC(=O)N1CCN(c2ccc3cnn(-c4cccc(C)c4)c3c2)CC1] | 2-(methylamino)-1-(4-(1-(m-tolyl)-1H-indazol-6-yl)piperazin-1-yl)ethan-1-one | 364 |
| C-12 | SPR371 | 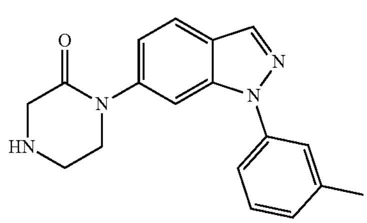 [SMILES: Cc1cccc(-n2ncc3ccc(N4CCNCC4=O)cc32)c1] | 1-(1-(m-tolyl)-1H-indazol-6-yl)piperazin-2-one | 307 |

TABLE 1-continued

| Compound | TEMP SPR CROSS REF | Structure | IUPAC Name | M/Z |
|---|---|---|---|---|
| C-13 | SPR341 | 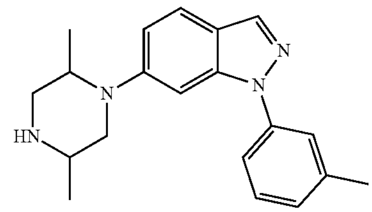 [SMILES: Cc1cccc(-n2ncc3ccc(N4CC(C)NCC4C)cc32)c1] | 6-(2,5-dimethylpiperazin-1-yl)-1-(m-tolyl)-1H-indazole | 321 |
| C-14 | SPR343 | 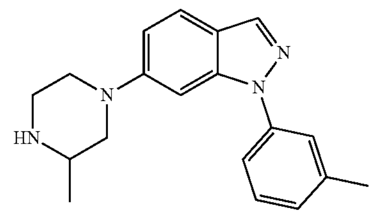 [SMILES: Cc1cccc(-n2ncc3ccc(N4CCNC(C)C4)cc32)c1] | 6-(3-methylpiperazin-1-yl)-1-(m-tolyl)-1H-indazole | 307 |
| C-15 | SPR344 | 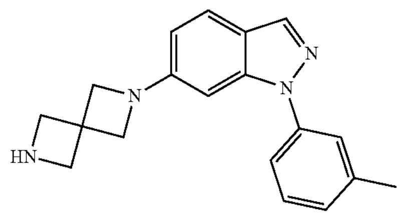 [SMILES: Cc1cccc(-n2ncc3ccc(N4CC5(CNC5)C4)cc32)c1] | 6-(2,6-diazaspiro[3.3]heptan-2-yl)-1-(m-tolyl)-1H-indazole | 305 |
| C-16 | SPR346 | 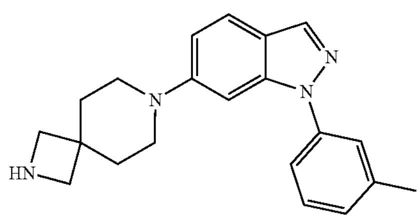 [SMILES: Cc1cccc(-n2ncc3ccc(N4CCC5(CC4)CNC5)cc32)c1] | 7-(1-(m-tolyl)-1H-indazol-6-yl)-2,7-diazaspiro[3.5]nonane | 333 |
| C-17 | SPR367 | 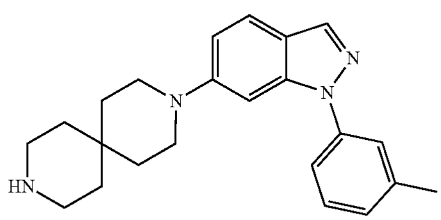 [SMILES: Cc1cccc(-n2ncc3ccc(N4CCC5(CCNCC5)CC4)cc32)c1] | 3-(1-(m-tolyl)-1H-indazol-6-yl)-3,9-diazaspiro[5.5]undecane | 261 |
| C-18 | SPR363 | 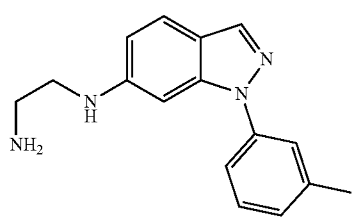 [SMILES: Cc1cccc(-n2ncc3ccc(NCCN)cc32)c1] | N1-(1-(m-tolyl)-1H-indazol-6-yl)ethane-1,2-diamine | 267 |
| C-19 | SPR336 | 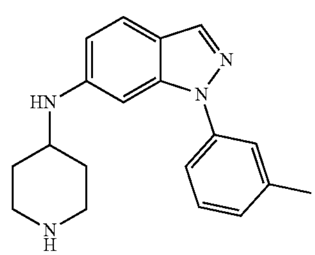 [SMILES: Cc1cccc(-n2ncc3ccc(NC4CCNCC4)cc32)c1] | N-(piperidin-4-yl)-1-(m-tolyl)-1H-indazol-6-amine | 307 |

TABLE 1-continued

| Compound | TEMP SPR CROSS REF | Structure | IUPAC Name | M/Z |
|---|---|---|---|---|
| C-20 | SPR369 | 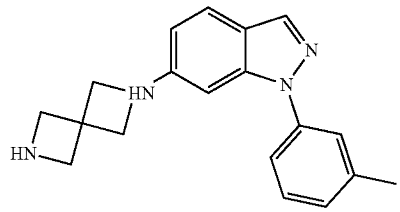 [SMILES: Cc1cccc(-n2ncc3ccc(N4CC5(CNC5)C4)cc32)c1] | N-(2-azaspiro[3.3]heptan-6-yl)-1-(m-tolyl)-1H-indazol-6-amine | 319 |
| C-21 | SPR358 | 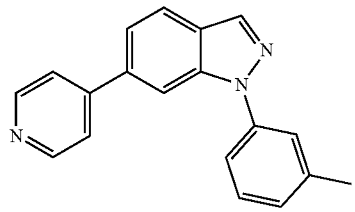 [SMILES: Cc1cccc(-n2ncc3ccc(-c4ccncc4)cc32)c1] | 6-(pyridin-4-yl)-1-(m-tolyl)-1H-indazole | 286 |
| C-22 | SPR355 | 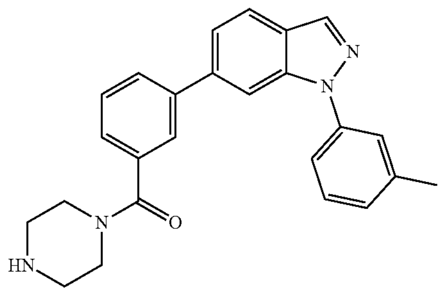 [SMILES: Cc1cccc(-n2ncc3ccc(-c4cccc(C(=O)N5CCNCC5)c4)cc32)c1] | piperazin-1-yl(3-(1-(m-tolyl)-1H-indazol-6-yl)phenyl)methanone | 397 |
| C-23 | SPR357 | 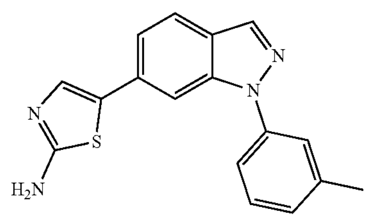 [SMILES: Cc1cccc(-n2ncc3ccc(-c4cnc(N)s4)cc32)c1] | 5-(1-(m-tolyl)-1H-indazol-6-yl)thiazol-2-amine | 307 |
| C-24 | SPR368 | 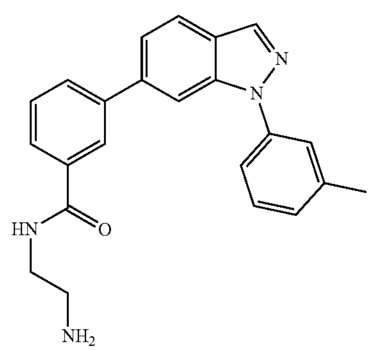 [SMILES: Cc1cccc(-n2ncc3ccc(-c4cccc(C(=O)NCCN)c4)cc32)c1] | N-(2-aminoethyl)-3-(1-(m-tolyl)-1H-indazol-6-yl)benzamide | 371 |
| C-25 | SPR379 | 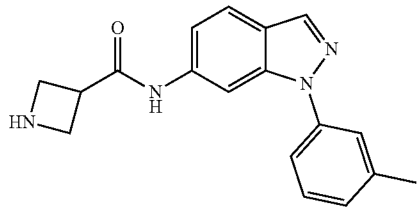 [SMILES: Cc1cccc(-n2ncc3ccc(NC(=O)C4CNC4)cc32)c1] | N-(1-(m-tolyl)-1H-indazol-6-yl)azetidine-3-carboxamide | 307 |

TABLE 1-continued

| Compound | TEMP SPR CROSS REF | Structure | IUPAC Name | M/Z |
|---|---|---|---|---|
| C-26 | SPR437 | 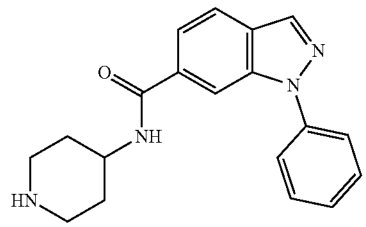 [SMILES: O=C(NC1CCNCC1)c1ccc2cnn(-c3ccccc3)c2c1] | 1-phenyl-N-(piperidin-4-yl)-1H-indazole-6-carboxamide | 321 |
| C-27 | SPR406 | 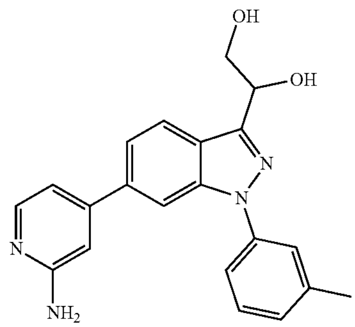 [SMILES: Cc1cccc(-n2nc(C(O)CO)c3ccc(-c4ccnc(N)c4)cc32)c1] | 1-(6-(2-aminopyridin-4-yl)-1-(m-tolyl)-1H-indazol-3-yl)ethane-1,2-diol | 361 |
| C-28 | SPR417 | 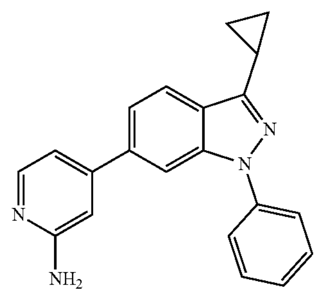 [SMILES: Nc1cc(-c2ccc3c(C4CC4)nn(-c4ccccc4)c3c2)ccn1] | 4-(3-cyclopropyl-1-phenyl-1H-indazol-6-yl)pyridin-2-amine | 327 |
| C-29 | SPR330 | 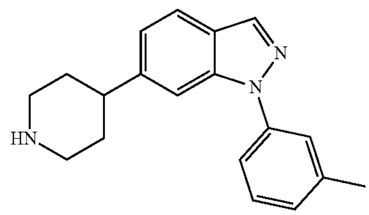 [SMILES: Cc1cccc(-n2ncc3ccc(C4CCNCC4)cc32)c1] | 6-(piperidin-4-yl)-1-(m-tolyl)-1H-indazole | 292 |
| C-30 | SPR327 | 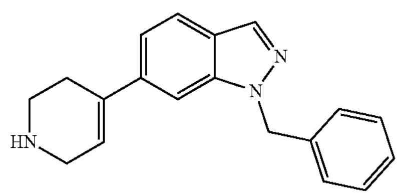 [SMILES: C1=C(c2ccc3cnn(Cc4ccccc4)c3c2)CCNC1] | 1-benzyl-6-(1,2,3,6-tetrahydropyridin-4-yl)-1H-indazole | 290 |
| C-31 | SPR364 | 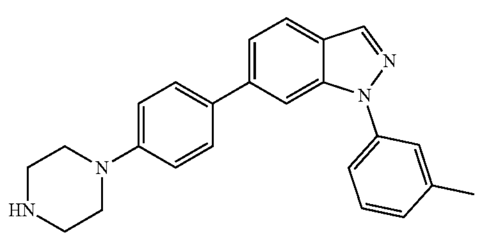 [SMILES: Cc1cccc(-n2ncc3ccc(-c4ccc(N5CCNCC5)cc4)cc32)c1] | 6-(4-(piperazin-1-yl)phenyl)-1-(m-tolyl)-1H-indazole | 369 |

TABLE 1-continued

| Compound | TEMP SPR CROSS REF | Structure | IUPAC Name | M/Z |
|---|---|---|---|---|
| C-32 | SPR435 | 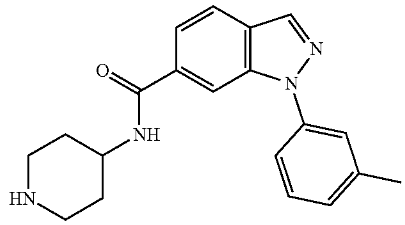 [SMILES: Cc1cccc(-n2ncc3ccc(C(=O)NC4CCNCC4)cc32)c1] | N-(piperidin-4-yl)-1-(m-tolyl)-1H-indazole-6-carboxamide | 335 |
| C-33 | SPR436 | 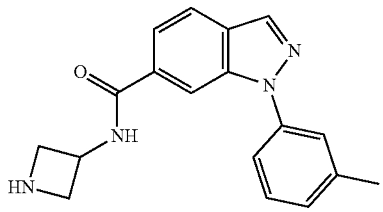 [SMILES: Cc1cccc(-n2ncc3ccc(C(=O)NC4CNC4)cc32)c1] | N-(azetidin-3-yl)-1-(m-tolyl)-1H-indazole-6-carboxamide | 307 |
| C-34 | SPR438 | 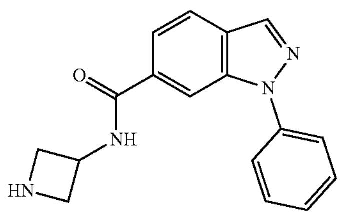 [SMILES: O=C(NC1CNC1)c1ccc2cnn(-c3ccccc3)c2c1] | N-(azetidin-3-yl)-1-phenyl-1H-indazole-6-carboxamide | 293 |
| C-35 | SPR490 | 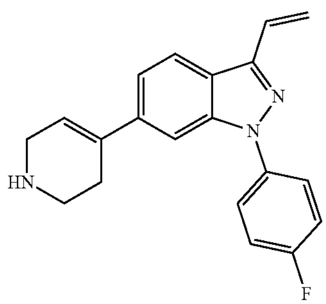 [SMILES: C=Cc1nn(-c2ccc(F)cc2)c2cc(C3=CCNCC3)ccc12] | 1-(4-fluorophenyl)-6-(1,2,3,6-tetrahydropyridin-4-yl)-3-vinyl-1H-indazole | 320 |
| C-36 | | 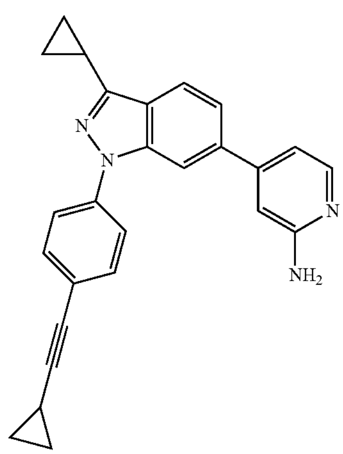 [SMILES: Nc1cc(-c2ccc3c(C4CC4)nn(-c4ccc(C#CC5CC5)cc4)c3c2)ccn1] | 4-(3-cyclopropyl-1-(4-(cyclopropylethynyl)phenyl)-1H-indazol-6-yl)pyridin-2-amine | 390 |

TABLE 1-continued

| Compound | TEMP SPR CROSS REF | Structure | IUPAC Name | M/Z |
|---|---|---|---|---|
| C-37 | | 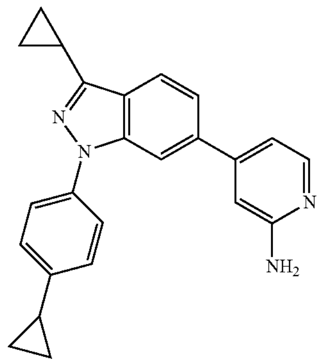 [SMILES: Nc1cc(-c2ccc3c(C4CC4)nn(-c4ccc(C5CC5)cc4)c3c2)ccn1] | 4-(3-cyclopropyl-1-(4-cyclopropylphenyl)-1H-indazol-6-yl)pyridin-2-amine | 366 |
| C-38 | | 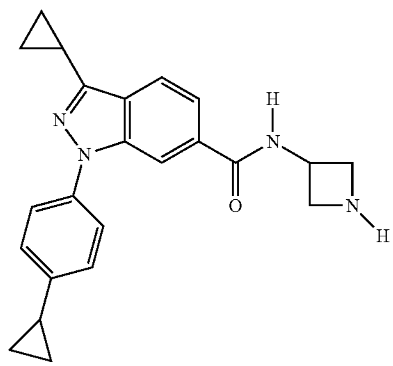 [SMILES: O=C(NC1CNC1)c1ccc2c(C3CC3)nn(-c3ccc(C4CC4)cc3)c2c1] | N-(azetidin-3-yl)-3-cyclopropyl-1-(4-cyclopropylphenyl)-1Hindazole-6-carboxamide | 372 |
| C-39 | | 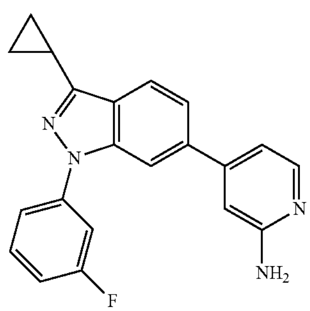 [SMILES: Nc1cc(-c2ccc3c(C4CC4)nn(-c4cccc(F)c4)c3c2)ccn1] | 4-(3-cyclopropyl-1-(3-fluorophenyl)-1H-indazol-6-yl)pyridin-2-amine | 344 |
| C-40 | | 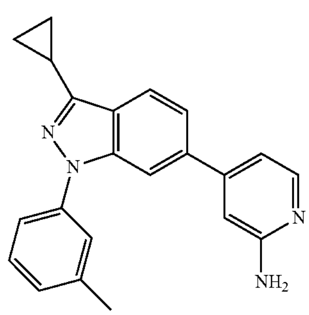 [SMILES: Cc1cccc(-n2nc(C3CC3)c3ccc(-c4ccnc(N)c4)cc32)c1] | 4-(3-cyclopropyl-1-(m-tolyl)-1H-indazol-6-yl)pyridin-2-amine | 340 |

TABLE 1-continued

| Compound | TEMP SPR CROSS REF | Structure | IUPAC Name | M/Z |
|---|---|---|---|---|
| C-41 | | 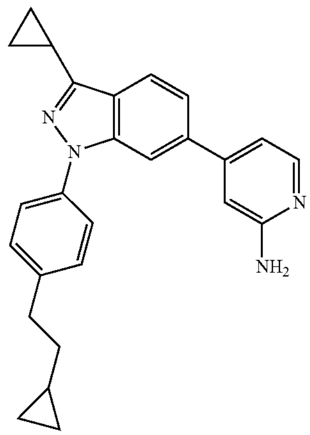 [SMILES: Nc1cc(-c2ccc3c(C4CC4)nn(-c4ccc(CCC5CC5)cc4)c3c2)ccn1] | 4-(3-cyclopropyl-1-(4-(2-cyclopropylethyl)phenyl)-1Hindazol-6-yl)pyridin-2-amine | 395 |
| C-42 | | 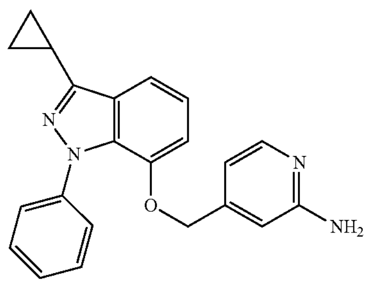 [SMILES: Nc1cc(COc2cccc3c(C4CC4)nn(-c4ccccc4)c23)ccn1] | 4-(((3-cyclopropyl-1-phenyl-1H-indazol-7-yl)oxy)methyl)pyridin-2-amine | 356 |
| C-43 | | 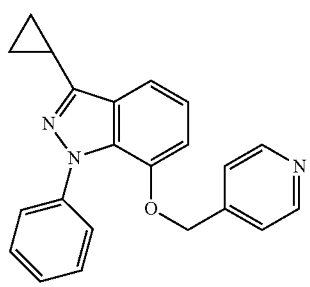 [SMILES: c1ccc(-n2nc(C3CC3)c3cccc(OCc4ccncc4)c32)cc1] | 3-cyclopropyl-1-phenyl-7-(pyridin-4-ylmethoxy)-1Hindazole | 341 |
| C-44 | | 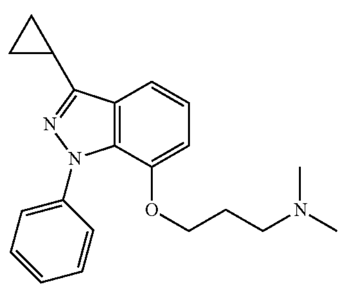 [SMILES: CN(C)CCCOc1cccc2c(C3CC3)nn(-c3ccccc3)c12] | 3-((3-cyclopropyl-1-phenyl-1H-indazol-7-yl)oxy)-N,Ndimethylpropan-1-amine | 335 |
| C-45 | | 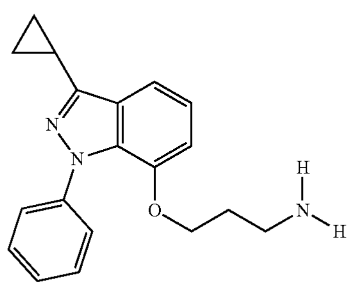 [SMILES: NCCCOc1cccc2c(C3CC3)nn(-c3ccccc3)c12] | 3-((3-cyclopropyl-1-phenyl-1H-indazol-7-yl)oxy)propan-1-amine | 307 |

TABLE 1-continued

| Compound | TEMP SPR CROSS REF | Structure | IUPAC Name | M/Z |
|---|---|---|---|---|
| C-46 | | 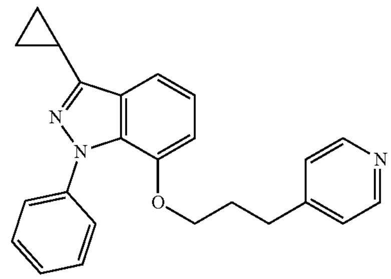 [SMILES: c1ccc(-n2nc(C3CC3)c3cccc(OCCCc4ccncc4)c32)cc1] | 3-cyclopropyl-1-phenyl-7-(3-(pyridin-4-yl)propoxy)-1H-indazole | 369 |
| C-47 | | 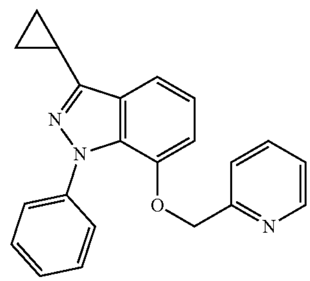 [SMILES: c1ccc(-n2nc(C3CC3)c3cccc(OCc4ccccn4)c32)cc1] | 3-cyclopropyl-1-phenyl-7-(pyridin-2-ylmethoxy)-1H-indazole | 341 |
| C-48 | | 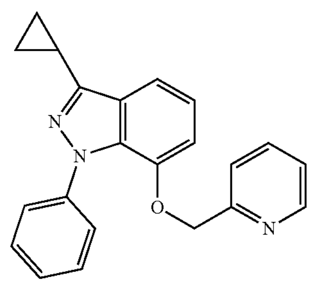 [SMILES: c1ccc(-n2nc(C3CC3)c3cccc(OCc4ccccn4)c32)cc1] | 2-((3-cyclopropyl-1-phenyl-1H-indazol-7-yl)oxy)-N,Ndimethylethan-1-amine | 321 |
| C-49 | | 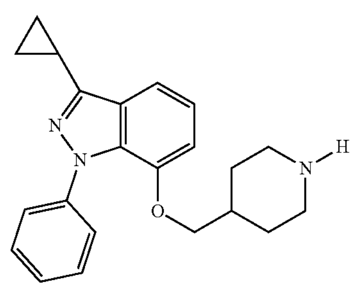 [SMILES: c1ccc(-n2nc(C3CC3)c3cccc(OCC4CCNCC4)c32)cc1] | 3-cyclopropyl-1-phenyl-7-(piperidin-4-ylmethoxy)-1Hindazole | 347 |
| C-50 | | 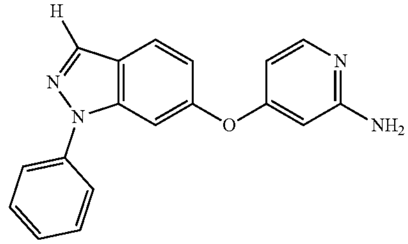 [SMILES: Nc1cc(Oc2ccc3cnn(-c4ccccc4)c3c2)ccn1] | 4-((1-phenyl-1H-indazol-6-yl)oxy)pyridin-2-amine | 302 |

TABLE 1-continued

| Compound | TEMP SPR CROSS REF | Structure | IUPAC Name | M/Z |
|---|---|---|---|---|
| C-51 | | 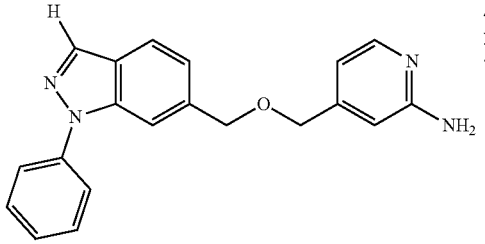 | 4-(((1-phenyl-1H-indazol-6-yl)methoxy)methyl)pyridin-2-amine | 330 |
| C-52 | | 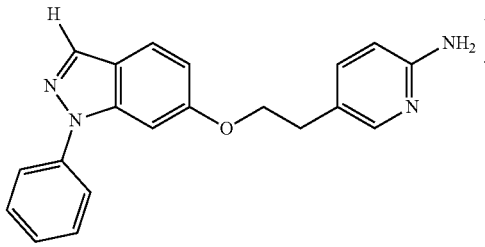 | 5-(2-((1-phenyl-1H-indazol-6-yl)oxy)ethyl)pyridin-2-amine | 330 |
| C-53 | | 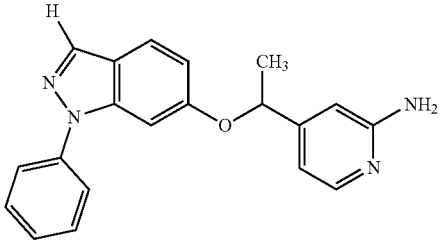 [SMILES: CC(Oc1ccc2cnn(-c3ccccc3)c2c1)c1ccnc(N)c1] | 4-(1-((1-phenyl-1H-indazol-6-yl)oxy)ethyl)pyridin-2-amine | 330 |
| C-54 | | 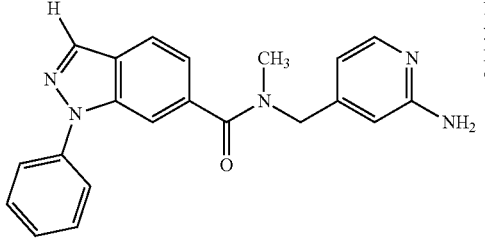 | N-((2-aminopyridin-4-yl)methyl)-N-methyl-1-phenyl-1H-indazole-6-carboxamide | 357 |
| C-55 | | 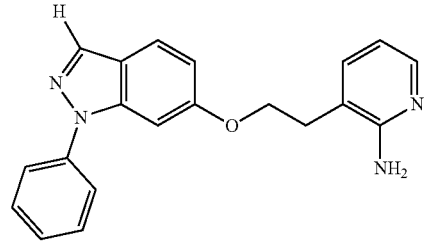 [SMILES: Nc1ncccc1CCOc1ccc2cnn(-c3ccccc3)c2c1] | 3-(2-((1-phenyl-1H-indazol-6-yl)oxy)ethyl)pyridin-2-amine | 330 |
| C-56 | | 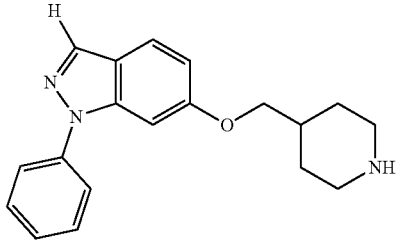 [SMILES: c1ccc(-n2ncc3ccc(OCC4CCNCC4)cc32)cc1] | 1-phenyl-6-(piperidin-4-ylmethoxy)-1H-indazole | 307 |

TABLE 1-continued

| Compound | TEMP SPR CROSS REF | Structure | IUPAC Name | M/Z |
|---|---|---|---|---|
| C-57 | | 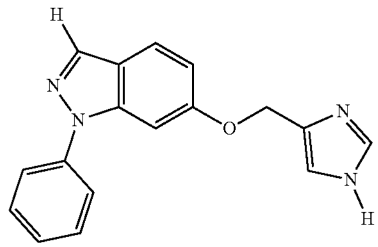 [SMILES: c1ccc(-n2ncc3ccc(OCc4c[nH]cn4)cc32)cc1] | 6-((1H-imidazol-4-yl)methoxy)-1-phenyl-1Hindazole | 290 |
| C-58 | | 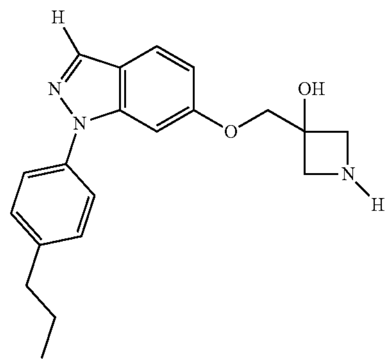 [SMILES: CCCc1ccc(-n2ncc3ccc(OCC4(O)CNC4)cc32)cc1] | 3-(((1-(4-propylphenyl)-1Hindazol-6-yl)oxy)methyl)azetidin-3-ol | 337 |
| C-59 | | 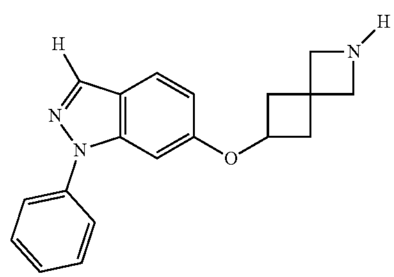 [SMILES: c1ccc(-n2ncc3ccc(OC4CC5(CNC5)C4)cc32)cc1] | 6-((2-azaspiro[3.3]heptan-6-yl)oxy)-1-phenyl-1H-indazole | 305 |
| C-60 | | 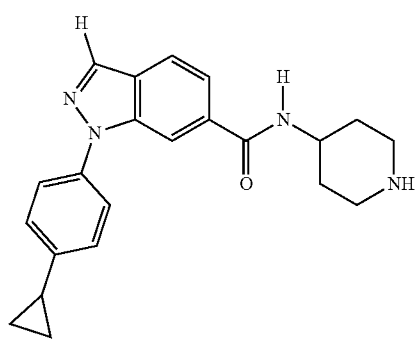 [SMILES: O=C(NC1CCNCC1)c1ccc2cnn(-c3ccc(C4CC4)cc3)c2c1] | 1-(4-cyclopropylphenyl)-N-(piperidin-4-yl)-1H-indazole-6-carboxamide | 360 |
| C-61 | | 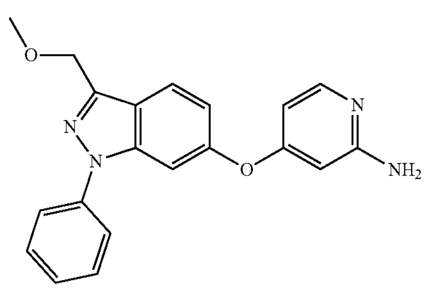 [SMILES: COCc1nn(-c2ccccc2)c2cc(Oc3ccnc(N)c3)ccc12] | 4-((3-(methoxymethyl)-1-phenyl-1H-indazol-6-yl)oxy)pyridin-2-amine | 346 |

TABLE 1-continued

| Compound | TEMP SPR CROSS REF | Structure | IUPAC Name | M/Z |
|---|---|---|---|---|
| C-62 | | 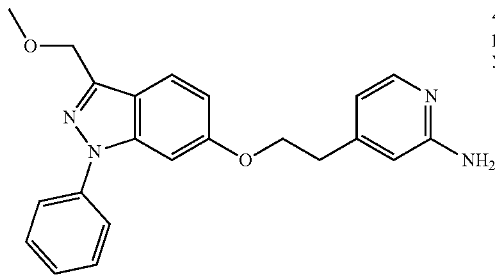 [SMILES: COCc1nn(-c2ccccc2)c2cc(OCCc3ccnc(N)c3)ccc12] | 4-(2-((3-(methoxymethyl)-1-phenyl-1H-indazol-6-yl)oxy)ethyl)pyridin-2-amine | 374 |
| C-63 | | 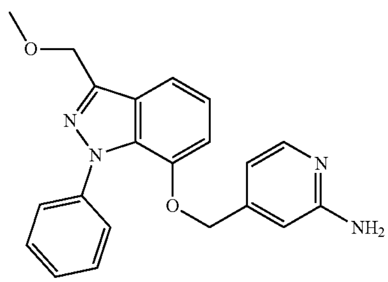 [SMILES: COCc1nn(-c2ccccc2)c2c(OCc3ccnc(N)c3)cccc12] | 4-(((3-(methoxymethyl)-1-phenyl-1H-indazol-7-yl)oxy)methyl)pyridin-2-amine | 360 |
| C-64 | | 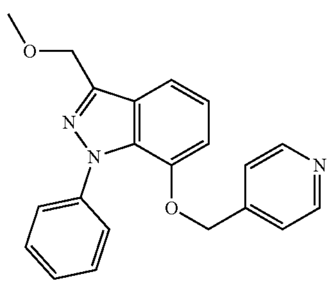 [SMILES: COCc1nn(-c2ccccc2)c2c(OCc3ccncc3)cccc12] | 3-(methoxymethyl)-1-phenyl-7-(pyridin-4-ylmethoxy)-1Hindazole | 345 |
| C-65 | | 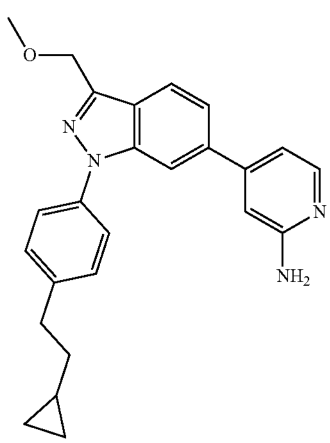 [SMILES: COCc1nn(-c2ccc(CCC3CC3)cc2)c2cc(-c3ccnc(N)c3)ccc12] | 4-(1-(4-(2-cyclopropylethyl)phenyl)-3-(methoxymethyl)-1H-indazol-6-yl)pyridin-2-amine | 398 |

TABLE 1-continued

| Compound | TEMP SPR CROSS REF | Structure | IUPAC Name | M/Z |
|---|---|---|---|---|
| C-66 | | 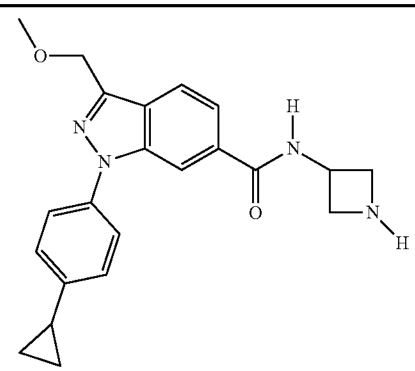 | N-(azetidin-3-yl)-1-(4-cyclopropylphenyl)-3-(methoxymethyl)-1Hindazole-6-carboxamide | 376 |
| C-67 | | 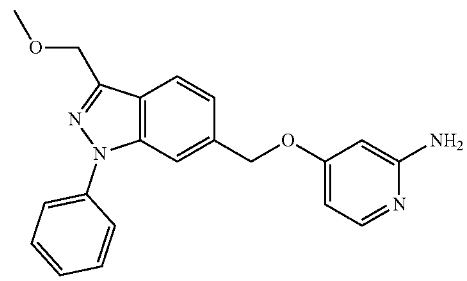 [SMILES: COCc1nn(-c2ccccc2)c2cc(COc3ccnc(N)c3)ccc12] | 4-((3-(methoxymethyl)-1-phenyl-1H-indazol-6-yl)methoxy)pyridin-2-amine | 360 |
| C-68 | | 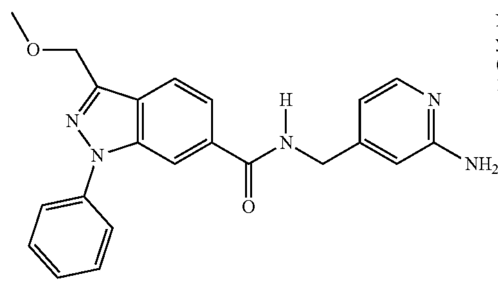 [SMILES: COCc1nn(-c2ccccc2)c2cc(C(=O)NCc3ccnc(N)c3)ccc12] | N-((2-aminopyridin-4-yl)methyl)-3-(methoxymethyl)-1-phenyl-1H-indazole-6-carboxamide | 387 |
| C-69 | | 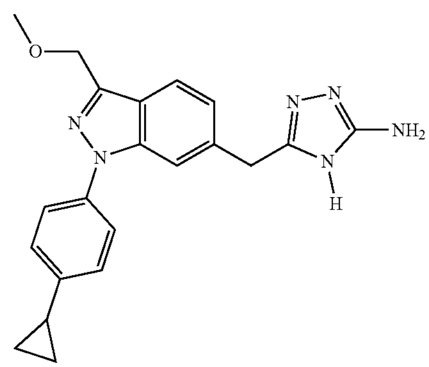 [SMILES: COCc1nn(-c2ccc(C3CC3)cc2)c2cc(Cc3nnc(N)[nH]3)ccc12] | 5-((1-(4-cyclopropylphenyl)-3-(methoxymethyl)-1Hindazol-6-yl)methyl)-4H-1,2,4-triazol-3-amine | 374 |
| C-70 | | 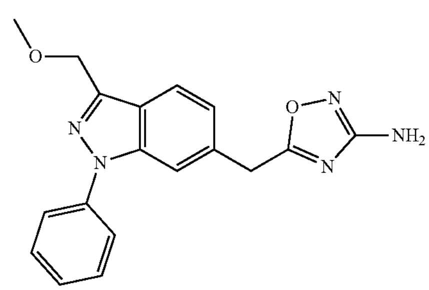 [SMILES: COCc1nn(-c2ccccc2)c2cc(Cc3nc(N)no3)ccc12] | 5-((3-(methoxymethyl)-1-phenyl-1H-indazol-6-yl)methyl)-1,2,4-oxadiazol-3-amine | 335 |

TABLE 1-continued

| Compound | TEMP SPR CROSS REF | Structure | IUPAC Name | M/Z |
|---|---|---|---|---|
| C-71 | SPR497 | 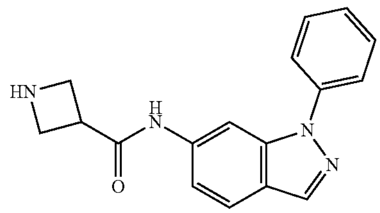 [SMILES: O=C(Nc1ccc2cnn(-c3ccccc3)c2c1)C1CNC1] | | |
| C-72 | SPR533 | 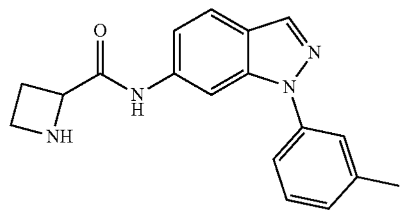 [SMILES: Cc1cccc(-n2ncc3ccc(NC(=O)C4CCN4)cc32)c1] | | |
| C73 | SPR535 | 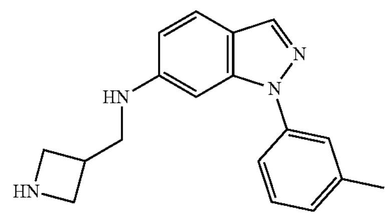 [SMILES: Cc1cccc(-n2ncc3ccc(NCC4CNC4)cc32)c1] | | |
| C74 | SPR539 | 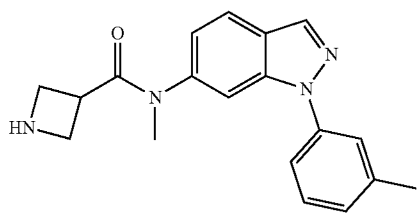 [SMILES: Cc1cccc(-n2ncc3ccc(N(C)C(=O)C4CNC4)cc32)c1] | | |

All of the foregoing are incorporated herein with respect to the teaching of KHK inhibitor molecules. Small molecule KHK inhibitors include those described above as well as pharmaceutically acceptable salt forms thereof, unless already described in the noted references.

Plant Extracts

Plant extracts that may be included as KHK inhibitors as described herein comprise a plant extract from one or more plants, or a combination of a plant extracts from one or more plants and an acceptable carrier, wherein the plant extract is obtained from a genus selected from the group consisting of *Angelica, Cratoxylum, Myrica, Psoralea, Scutellaria, Diospyros, Andrographis, Nymphaea, Chloroxylon, Petroselinum, Morus, Pteris, Garcinia,* and *Malus*, or a combination thereof. Examples of plant extracts that may serve as KHK inhibitors include those found in US Patent Pub 2014/0377386, incorporated herein by reference.

KHK RNA Interfering Molecules

KHK can be inhibited by a number of means including silencing via antisense, miRNA, shRNA, or siRNA, for example, which are various types of RNAi, directed to a portion of a KHK sequence, such as a nucleic acid sequence that encodes SEQ ID NO. 1 above, or that are described as genbank accession numbers NM_006488 (KHK-C) NM_000221 (KHK-A);

siRNA molecules can be prepared against a portion of KHK sequence according to the techniques provided in U.S Patent Publication 20060110440 and used as therapeutic compounds. Furthermore, KHK siRNAs are commercially available from, for example, ThermoFisher Scientific (catalog #AM16708) for example.

shRNA constructs are typically made from one of three possible methods; (i) annealed complementary oligonucleotides, (ii) promoter based PCR or (iii) primer extension. See Design and cloning strategies for constructing shRNA expression vectors, Glen J McIntyre, Gregory C Fanning BMC Biotechnology 2006, 6:1 (5 Jan. 2006).

For background information on the preparation of miRNA molecules, see e.g.. U.S. patent applications 20110020816, 2007/0099196; 2007/0099193; 2007/0009915; 2006/0130176; 2005/0277139; 2005/0075492; and 2004/0053411, the disclosures of which are hereby incorporated by reference herein. See also, U.S. Pat. Nos. 7,056,704 and 7,078,196 (preparation of miRNA molecules), incorporated by reference herein. Synthetic miRNAs are described in Vatolin, et al 2006 J Mol Biol 358, 983-6 and Tsuda, et al 2005 Int J Oncol 27, 1299-306, incorporated by reference herein.

Examples of RNA interfering molecules are provided in US20160340679, U.S. Pat. No. 9,387,245 and Softic et al. J Clin Invest. 2018 March 1; 128(3):1199.

KHK inhibitors may further include any KHK inhibitor being developed having a positive response in Phase IIa EBA trials, or any KHK inhibitor under development.

It is within the scope of aspects of the present invention to provide agents to silence KHK to achieve a therapeutic effect using interfering molecules.

EXAMPLES

Example 1—Alcohol Increases Hepatic Fructose Levels

As shown in FIG. 1A, mice were administered increasing amounts of alcohol in their drinking water, beginning with no alcohol (0%), then 3%, 6% and eventually 10% alcohol. Liver tissue was removed and found small levels of aldose reductase (AR) in the liver under normal (0% alcohol) conditions, but as alcohol intake increased, there was an upregulation of AR in the kidney relative to actin control (shown in both the Western blot and densitometry). AR is likely upregulated because alcohol can raise osmolality, which is known to increase AR expression (10), and it has been discovered herein that osmolality of ethanol containing solutions is increased with increasing ethanol intake (FIG. 1B). In turn, AR is known to raise sorbitol levels and can cause oxidative stress and inflammation resulting in liver injury (11). It has been discovered herein that the livers of ethanol treated mice have increased sorbitol levels (FIG. 1C).

Sorbitol can be converted to fructose by sorbitol dehydrogenase, and it has been found herein, that alcohol can stimulate fructose levels in the liver in mice that were receiving chow that did not include any significant quantities of fructose (FIG. 1D).

Example 2—Fructose Drives Alcohol Craving

Figure 2C:
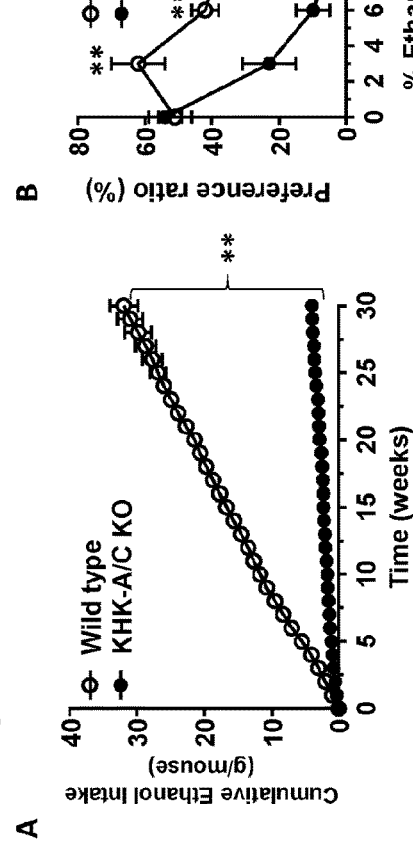
Figure 2D:
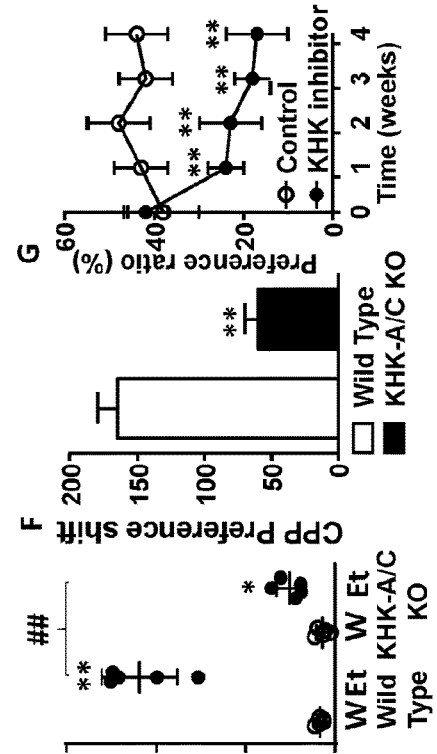
Figure 2E:
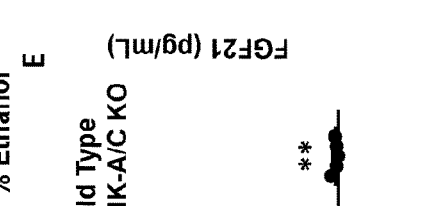

To understand the role of fructose in alcohol intake, alcohol was provided to either wild type control mice or mice that could not metabolize fructose (fructokinase knockout mice, KHK-A/C KO). The relative liking of alcohol was first evaluated by evaluating cumulative intake of alcohol in mice provided the choice of 10% ethanol or water for 30 weeks. As shown in FIG. 2A, KHK-A/C KO mice drank much less alcohol over the 30 week period. The preference ratio was also studied (preference of alcohol/water) in wild type and KHK-A/C KO mice over a 10 week period in which they were exposed stepwise to 3%, 6% and then 10% alcohol. As shown, wild type mice drank between 35 and 60 percent of their fluids as alcohol whereas KHK-A/C KO mice showed a stepwise decreased liking of alcohol over the 10 week period. FIG. 2C shows that delta FOSB, a transcription factor associated with addiction, was induced in the nucleus accumbens of wild type mice with increasing amounts of alcohol. In contrast, the induction of delta FosB by western analysis was blunted in KHK-A/C KO mice administered 10% alcohol compared to wild type mice (FIG. 2D). FIG. 2 also demonstrates that the lanes are equally loaded, based on the housekeeping protein, GAPDH, and that the KHK-A/C KO mice indeed lack KHK A/C in the liver. FGF-21 is a protein that is induced by alcohol and is thought to block alcohol craving. As shown in FIG. 2E, wild type mice given alcohol show an increase in FGF21 levels, but levels of FGF-21 are lower in the KHK-A/C KO mice.

Figure 2F:
FIG. 2F provides evidence of conditioned place preference in wild type and fructokinase knockout mice injected alcohol (2 g/kg). Data represents preference shifts for the paired section after vs before conditioning (time spent in the paired chamber posttest-pretest).
Figure 2G:
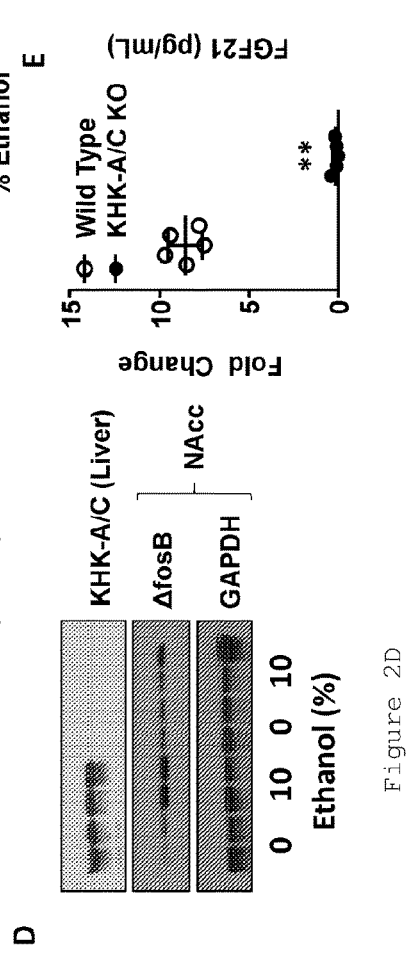
FIG. 2G shows alcohol preference in two-bottle choice preference paradigms in wild type control and fructokinase inhibitor exposed mice treated with water and 10% alcohol solutions for 4 weeks. $*p<0.05$ and $**p<0.01$ versus respective controls $\#\#p<0.01$. One Way ANOVA with Tukey post hoc analysis; n=5 mice per group.

Further evidence that KHK may mediate alcohol preference is shown by a conditioned place preference study, in which mice are injected with either alcohol or saline then placed in a distinctly different section of the apparatus for 4 alcohol and 4 saline trials. The mice were then tested in an alcohol-free state to determine whether they preferred the section of the apparatus that was paired with alcohol. As shown in FIG. 2F, a significantly attenuated preference shift was observed for KHK-A/C KO mice, as they showed much less preference for the room paired with alcohol than wild type mice. It was also determined that preference for alcohol could be blocked by administering a fructokinase inhibitor (i.e., osthol) for 4 weeks to wild type mice on 10 percent alcohol. As shown in FIG. 2G, the administration of a fructokinase inhibitor led to a reduced preference for alcohol in a two bottle preference system by 50 percent. Thus, these studies show the novel finding that blocking fructokinase can block the craving for alcohol.

Example 3—Fructose and Alcohol-Induced Liver Disease

The finding that alcohol can induce hepatic fructose levels raised the question that some of the liver disease from alcohol might actually be mediated by fructose-dependent fatty liver. To determine if blocking fructose metabolism could prevent alcohol induced fatty liver, wild type mice on 10% alcohol were compared with KHK-A/C KO mice on 20% alcohol for 30 weeks. KHK A/C KO mice drink half the amount of alcohol as wild type mice. Comparison allowed for the evaluation of the effects of equivalent alcohol intake between groups. As shown in FIG. 3A, wild type mice developed fatty liver demonstrated by the vacuoles containing fat whereas KHK A/C KO mice appeared protected from fatty liver. Furthermore, KHK A/C KO mice showed less hepatomegaly (liver weight) (FIG. 3B), hepatic triglyceride accumulation (FIG. 3C), transaminitis (FIGS. 3D and 3E), as well as activation of NFκB (as noted by p65 nuclear staining) (FIG. 3F), expression of inflammatory cytokine mRNA (FIG. 3G) and fibrosis (noted by picosirius red staining) (FIG. 3H). Thus, alcohol induced liver disease can be prevented by blocking fructokinase. In addition, because fructokinase blockade reduces craving for alcohol, fructokinase blockade also prevents alcohol associated liver disease by both reducing alcohol intake while also blocking alcohol liver injury via inhibition of fructose metabolism.

The novel findings described herein demonstrate that alcohol increases hepatic fructose levels, and blocking fructose metabolism blocks alcohol associated craving, alcohol associated addiction, and alcohol mediated liver disease.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference in their entirety to the extent they are not inconsistent with the teachings herein.

REFERENCES

1. Most D, Ferguson L, Harris R A. Molecular basis of alcoholism. Handb Clin Neurol. 2014; 125:89-111.
2. Gao B, Bataller R. Alcoholic liver disease: pathogenesis and new therapeutic targets. Gastroenterology. 2011; 141 (5):1572-85.
3. Beier J I, McClain C J. Mechanisms and cell signaling in alcoholic liver disease. Biol Chem. 2010; 391(11):1249-64.
4. Hajnal A, Smith G P, Norgren R. Oral sucrose stimulation increases accumbens dopamine in the rat. Am J Physiol Regul Integr Comp Physiol. 2004; 286(1):R31-7.
5. Rada P, Avena N M, Hoebel B G. Daily bingeing on sugar repeatedly releases dopamine in the accumbens shell. Neuroscience. 2005; 134(3):737-44.
6. Lustig R H. Fructose: it's "alcohol without the buzz". Adv Nutr. 2013; 4(2):226-35.
7. Westwater M L, Fletcher P C, Ziauddeen H. Sugar addiction: the state of the science. Eur J Nutr. 2016; 55(Suppl 2):55-69.
8. Jensen T, Abdelmalek M F, Sullivan S, Nadeau K J, Green M, Roncal C, et al. Fructose and sugar: A major mediator of non-alcoholic fatty liver disease. J Hepatol. 2018; 68(5):1063-75.
9. Thomes P G, Benbow J H, Brandon-Warner E, Thompson K J, Jacobs C, Donohue T M, Jr., et al. Dietary fructose augments ethanol-induced liver pathology. J Nutr Biochem. 2017; 43:141-50.
10. Ko B C, Ruepp B, Bohren K M, Gabbay K H, Chung S S. Identification and characterization of multiple osmotic response sequences in the human aldose reductase gene. J Biol Chem. 1997; 272(26):16431-7.
11. Tang W H, Martin K A, Hwa J. Aldose reductase, oxidative stress, and diabetic mellitus. Front Pharmacol. 2012; 3:87.
12. Brown K E, Broadhurst K A, Mathahs M M, Kladney R D, Fimmel C J, Srivastava S K, et al. Immunodetection of aldose reductase in normal and diseased human liver. Histol Histopathol. 2005; 20(2):429-36.
13. Shi C, Wang Y, Gao J, Chen S, Zhao X, Cai C, et al. Inhibition of aldose reductase ameliorates alcoholic liver disease by activating AMPK and modulating oxidative stress and inflammatory cytokines. Mol Med Rep. 2017; 16(3):2767-72.
14. Maryanoff B E, O'Neill J C, McComsey D F, Yabut S C, Luci D K, Gibbs A C, et al. Pyrimidinopyrimidine inhibitors of ketohexokinase: exploring the ring C2 group that interacts with Asp-27B in the ligand binding pocket. Bioorg Med Chem Lett. 2012; 22(16):5326-9.
15. Maryanoff B E, O'Neill J C, McComsey D F, Yabut S C, Luci D K, Jordan A D, et al. Inhibitors of Ketohexokinase: Discovery of Pyrimidinopyrimidines with Specific Substitution that Complements the ATP-Binding Site. ACS Med Chem Lett. 2011; 2:538-43.
16. Gibbs A C, Abad M C, Zhang X, Tounge B A, Lewandowski F A, Struble G T, et al. Electron density guided fragment-based lead discovery of ketohexokinase inhibitors. J Med Chem. 2010; 53(22):7979-91.
17. Zhang X, Song F, Kuo G H, Xiang A, Gibbs A C, Abad M C, et al. Optimization of a pyrazole hit from FBDD into a novel series of indazoles as ketohexokinase inhibitors. Bioorg Med Chem Lett. 2011; 21(16):4762-7.
18. Le M T, Lanaspa M A, Cicerchi C M, Rana J, Scholten J D, Hunter B L, et al. Bioactivity-Guided Identification of Botanical Inhibitors of Ketohexokinase. PLoS One. 2016; 11(6):e0157458.
19. Huard K, Ahn K, Amor P, Beebe D A, Borzilleri K A, Chrunyk B A, et al. Discovery of Fragment-Derived Small Molecules for in Vivo Inhibition of Ketohexokinase (KHK). J Med Chem. 2017; 60(18):7835-49.
20. Softic S, Gupta M K, Wang G X, Fujisaka S, O'Neill B T, Rao T N, et al. Divergent effects of glucose and fructose on hepatic lipogenesis and insulin signaling. J Clin Invest. 2018; 128(3):1199.
21. Softic S, Gupta M K, Wang G X, Fujisaka S, O'Neill B T, Rao T N, et al. Divergent effects of glucose and fructose on hepatic lipogenesis and insulin signaling. J Clin Invest. 2017; 127(11):4059-74.

What is claimed is:

1. A method of treating alcohol addiction in a subject determined to have alcohol addiction, comprising:
    administering a therapeutically effective amount of a ketohexokinase (KHK) inhibitor to the subject to inhibit KHK activity in the subject, wherein the KHK inhibitor is a small molecule KHK inhibitor that inhibits KHK activity; wherein administering is via an oral route; and wherein the therapeutically effective amount is at a dose of 0.001 mg/kg to about 100 mg/kg.

2. A method of treating alcoholism in a subject in need thereof, the method comprising:
    administering to the subject a therapeutically effective amount of a ketohexokinase (KHK) inhibitor, wherein the KHK inhibitor is a small molecule KHK inhibitor that inhibits KHK activity; wherein administering is via an oral route; and wherein the therapeutically effective amount is at a dose of 0.001 mg/kg to about 100 mg/kg.

* * * * *

UNITED STATES PATENT AND TRADEMARK OFFICE
CERTIFICATE OF CORRECTION

PATENT NO. : 12,161,621 B2
APPLICATION NO. : 17/261279
DATED : December 10, 2024
INVENTOR(S) : Richard J. Johnson et al.

It is certified that error appears in the above-identified patent and that said Letters Patent is hereby corrected as shown below:

On the Title Page

Item (73), Lines 1-2, "THE REGENTS OF THE UNIVERSITY OF COLORADO" should be
-- THE REGENTS OF THE UNIVERSITY OF COLORADO, Denver, CO (US) --.

Item (57), Line 5, "including a" should be -- including --.

Signed and Sealed this
Tenth Day of June, 2025

Coke Morgan Stewart
*Acting Director of the United States Patent and Trademark Office*